(12) United States Patent
Hu

(10) Patent No.: US 11,965,176 B2
(45) Date of Patent: Apr. 23, 2024

(54) MODIFICATION OF IMMUNE CELLS FOR REDUCING TOXICITY AND USES THEREOF IN ADOPTIVE CELL THERAPY

(71) Applicant: HUNAN SIWEIKANG THERAPEUTICS CO. LTD, Hunan (CN)

(72) Inventor: Biliang Hu, Worcester, MA (US)

(73) Assignee: HUNAN SIWEIKANG THERAPEUTICS CO. LTD, Changsha (CN)

( * ) Notice: Subject to any disclaimer, the term of this patent is extended or adjusted under 35 U.S.C. 154(b) by 557 days.

(21) Appl. No.: 16/980,237

(22) PCT Filed: Mar. 13, 2019

(86) PCT No.: PCT/US2019/022093
§ 371 (c)(1),
(2) Date: Sep. 11, 2020

(87) PCT Pub. No.: WO2019/178259
PCT Pub. Date: Sep. 19, 2019

(65) Prior Publication Data
US 2021/0009951 A1 Jan. 14, 2021

Related U.S. Application Data

(60) Provisional application No. 62/642,821, filed on Mar. 14, 2018.

(51) Int. Cl.
| | |
|---|---|
| C07K 14/525 | (2006.01) |
| C07K 14/475 | (2006.01) |
| C07K 14/52 | (2006.01) |
| C07K 14/53 | (2006.01) |
| C07K 14/54 | (2006.01) |
| C07K 14/705 | (2006.01) |
| C07K 16/18 | (2006.01) |
| C07K 16/24 | (2006.01) |
| C12N 5/078 | (2010.01) |
| C12N 5/0783 | (2010.01) |
| C12N 5/16 | (2006.01) |
| C12N 15/63 | (2006.01) |

(52) U.S. Cl.
CPC .......... *C12N 5/0634* (2013.01); *C07K 14/475* (2013.01); *C07K 14/52* (2013.01); *C07K 14/525* (2013.01); *C07K 14/53* (2013.01); *C07K 14/54* (2013.01); *C07K 14/705* (2013.01); *C07K 16/18* (2013.01); *C07K 16/248* (2013.01); *C12N 5/16* (2013.01); *C12N 15/63* (2013.01); *C07K 2317/24* (2013.01); *C07K 2317/622* (2013.01); *C12N 2310/10* (2013.01); *C12N 2310/11* (2013.01); *C12N 2310/14* (2013.01); *C12N 2310/20* (2017.05)

(58) Field of Classification Search
CPC .... C12N 5/0634; C12N 5/10; C12N 2310/20; C12N 2310/10; C12N 2310/14; C12N 15/63; C07K 14/52; C07K 14/475; C07K 14/705; C07K 16/28; C07K 2319/03; C07K 2317/24; C07K 2317/622
See application file for complete search history.

(56) References Cited

U.S. PATENT DOCUMENTS

| | | | |
|---|---|---|---|
| 2012/0149880 A1 | 6/2012 | Cheung et al. | |
| 2013/0122003 A1 | 5/2013 | Zhang et al. | |
| 2016/0289637 A1* | 10/2016 | Goldberg | C12N 15/102 |
| 2018/0155715 A1* | 6/2018 | Bowles | A61P 19/02 |
| 2019/0194343 A1* | 6/2019 | Durrant | C07K 16/243 |

FOREIGN PATENT DOCUMENTS

| | | | |
|---|---|---|---|
| CA | 3093518 A1 | 10/2019 | |
| WO | WO 2014/011984 A1 | 1/2014 | |
| WO | WO 2017/123556 A1 | 7/2017 | |
| WO | WO-2017117521 A1 * | 7/2017 | |
| WO | WO 2017/136820 A2 | 8/2017 | |
| WO | WO 2017/172981 A2 | 10/2017 | |
| WO | WO 2017/202387 A1 | 11/2017 | |
| WO | WO 2018/042385 A2 | 3/2018 | |

OTHER PUBLICATIONS

Bonifant et al. Toxicity and management in CAR T-cell therapy. Mol Ther-Oncolytics 3: 16011, 2016 (7 total pages).*
Doudna, J.A. The promise and challenge of therapeutic genome editing. Nature 578: 229-236, 2020.*
Godel et al. Understanding cytokine release syndrome. Intestive Care Med 44: 371-373, 2018.*
Khalil, A.M. The genome editing revolution: review. J Genetic Eng Biotechnol 18: 68, 2020 (16 total pages).*
Khan, S.H. Genome-editing technologies: concept, pros, and cons of various genome-editing techniques and bioethical concerns for clinical application. Mol Ther Nucleic Acids16: 326-334, 2019.*
Porteus, M. Genome editing: a new approach to human therapeutics. Annu Rev Pharmacol Toxicol 56: 163-190, 2016.*
Shimabukuro-Vornhagen et al. Cytokine release syndrome. J Immunother Cancer 6: 56, 2018 (14 total pages).*

(Continued)

*Primary Examiner* — Bridget E Bunner
(74) *Attorney, Agent, or Firm* — Mintz, Levin, Cohn, Ferris, Glovsky and Popeo, P.C.

(57) ABSTRACT

A population of immune cells comprising modified immune cells with reduced inflammatory properties, wherein such modified immune cells may have reduced production of one or more inflammatory cytokines (e.g., interleukin 2) and/or express one or more antagonists of one or more inflammatory cytokines (e.g., interleukin 6). Also provided herein are methods of producing such immune cell populations comprising the modified immune cells and methods of using such in cell therapy (e.g., to treat cancer, infectious diseases or immune diseases).

15 Claims, 5 Drawing Sheets

Specification includes a Sequence Listing.

(56) References Cited

OTHER PUBLICATIONS

Becher, Burkhard, et al. "Experimental autoimmune encephalitis and inflammation in the absence of interleukin-12." The Journal of Clinical Investigation, vol. 110, No. 4, pp. 493-497, 2002.

Furtado, Gláucia C., et al. "Interleukin 2 signaling is required for CD4+ regulatory T cell function." The Journal of Experimental Medicine, vol. 196, No. 6, pp. 851-857, 2002.

* cited by examiner

SEQUENCE LISTING

<160> NUMBER OF SEQ ID NOS: 94

<210> SEQ ID NO 1
<211> LENGTH: 20
<212> TYPE: DNA
<213> ORGANISM: Homo sapiens

<400> SEQUENCE: 1
gctgcagagc ctgctgctct                                               20

<210> SEQ ID NO 2
<211> LENGTH: 20
<212> TYPE: DNA
<213> ORGANISM: Homo sapiens

<400> SEQUENCE: 2
ggagcatgtg aatgccatcc                                               20

<210> SEQ ID NO 3
<211> LENGTH: 20
<212> TYPE: DNA
<213> ORGANISM: Homo sapiens

<400> SEQUENCE: 3
gcatgtgaat gccatccagg                                               20

<210> SEQ ID NO 4
<211> LENGTH: 20
<212> TYPE: DNA
<213> ORGANISM: Homo sapiens

<400> SEQUENCE: 4
gagacgccgg gcctcctgga                                               20

<210> SEQ ID NO 5
<211> LENGTH: 20
<212> TYPE: DNA
<213> ORGANISM: Homo sapiens

<400> SEQUENCE: 5
gatggcattc acatgctccc                                               20

<210> SEQ ID NO 6
<211> LENGTH: 20
<212> TYPE: DNA
<213> ORGANISM: Homo sapiens

<400> SEQUENCE: 6
gctcccaggg ctgcgtgctg                                               20

<210> SEQ ID NO 7
<211> LENGTH: 20
<212> TYPE: DNA
<213> ORGANISM: Homo sapiens

<400> SEQUENCE: 7
gcgtgctggg gctgggcgag                                               20

<210> SEQ ID NO 8
<211> LENGTH: 20
<212> TYPE: DNA
<213> ORGANISM: Homo sapiens

<400> SEQUENCE: 8

| | |
|---|---|
| gctggggctg ggcgagcggg | 20 |

<210> SEQ ID NO 9
<211> LENGTH: 20
<212> TYPE: DNA
<213> ORGANISM: Homo sapiens

<400> SEQUENCE: 9

| | |
|---|---|
| gacttagtgc aatgcaagac | 20 |

<210> SEQ ID NO 10
<211> LENGTH: 20
<212> TYPE: DNA
<213> ORGANISM: Homo sapiens

<400> SEQUENCE: 10

| | |
|---|---|
| gatttacaga tgattttgaa | 20 |

<210> SEQ ID NO 11
<211> LENGTH: 19
<212> TYPE: DNA
<213> ORGANISM: Homo sapiens

<400> SEQUENCE: 11

| | |
|---|---|
| aagaaaacac agctacaac | 19 |

<210> SEQ ID NO 12
<211> LENGTH: 19
<212> TYPE: DNA
<213> ORGANISM: Homo sapiens

<400> SEQUENCE: 12

| | |
|---|---|
| caactggagc atttactgc | 19 |

<210> SEQ ID NO 13
<211> LENGTH: 19
<212> TYPE: DNA
<213> ORGANISM: Homo sapiens

<400> SEQUENCE: 13

| | |
|---|---|
| tctttgtaga acttgaagt | 19 |

<210> SEQ ID NO 14
<211> LENGTH: 20
<212> TYPE: DNA
<213> ORGANISM: Homo sapiens

<400> SEQUENCE: 14

| | |
|---|---|
| gagcactgaa agcatgatcc | 20 |

<210> SEQ ID NO 15
<211> LENGTH: 20
<212> TYPE: DNA
<213> ORGANISM: Homo sapiens

<400> SEQUENCE: 15

| | |
|---|---|
| ggacgtggag ctggccgagg | 20 |

<210> SEQ ID NO 16
<211> LENGTH: 20
<212> TYPE: DNA
<213> ORGANISM: Homo sapiens

```
<400> SEQUENCE: 16
gaggcgctcc ccaagaagac                                               20

<210> SEQ ID NO 17
<211> LENGTH: 20
<212> TYPE: DNA
<213> ORGANISM: Homo sapiens

<400> SEQUENCE: 17
gggggcccca gggctccagg                                               20

<210> SEQ ID NO 18
<211> LENGTH: 20
<212> TYPE: DNA
<213> ORGANISM: Homo sapiens

<400> SEQUENCE: 18
gctgaggaac aagcaccgcc                                               20

<210> SEQ ID NO 19
<211> LENGTH: 20
<212> TYPE: DNA
<213> ORGANISM: Homo sapiens

<400> SEQUENCE: 19
ggcgcctgcc acgatcagga                                               20

<210> SEQ ID NO 20
<211> LENGTH: 20
<212> TYPE: DNA
<213> ORGANISM: Homo sapiens

<400> SEQUENCE: 20
gtgcagcagg cagaagagcg                                               20

<210> SEQ ID NO 21
<211> LENGTH: 19
<212> TYPE: DNA
<213> ORGANISM: Homo sapiens

<400> SEQUENCE: 21
ggagtgatcg gcccccaga                                                19

<210> SEQ ID NO 22
<211> LENGTH: 240
<212> TYPE: PRT
<213> ORGANISM: Artificial Sequence
<220> FEATURE:
<223> OTHER INFORMATION: Synthetic polypeptide

<400> SEQUENCE: 22
```

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ile Ser Val Ser Tyr Met
            20                  25                  30

Tyr Trp Tyr Gln Gln Lys Pro Gly Gln Ala Pro Arg Leu Leu Ile Tyr
        35                  40                  45

Asp Met Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

```
Asp Phe Ala Val Tyr Tyr Cys Met Gln Trp Ser Gly Tyr Pro Tyr Thr
                85                  90                  95

Phe Gly Gly Gly Thr Lys Val Glu Ile Lys Gly Gly Gly Gly Ser Gly
            100                 105                 110

Gly Gly Gly Ser Gly Gly Gly Ser Glu Val Gln Leu Val Glu Ser
        115                 120                 125

Gly Gly Gly Leu Val Gln Pro Gly Gly Ser Leu Arg Leu Ser Cys Ala
        130                 135                 140

Ala Ser Gly Phe Thr Phe Ser Pro Phe Ala Met Ser Trp Val Arg Gln
145                 150                 155                 160

Ala Pro Gly Lys Gly Leu Glu Trp Val Ala Lys Ile Ser Pro Gly Gly
                165                 170                 175

Ser Trp Thr Tyr Tyr Ser Asp Thr Val Thr Gly Arg Phe Thr Ile Ser
                180                 185                 190

Arg Asp Asn Ala Lys Asn Ser Leu Tyr Leu Gln Met Asn Ser Leu Arg
                195                 200                 205

Ala Glu Asp Thr Ala Val Tyr Tyr Cys Ala Arg Gln Leu Trp Gly Tyr
            210                 215                 220

Tyr Ala Leu Asp Ile Trp Gly Gln Gly Thr Thr Val Thr Val Ser Ser
225                 230                 235                 240

<210> SEQ ID NO 23
<211> LENGTH: 26
<212> TYPE: PRT
<213> ORGANISM: Homo sapiens

<400> SEQUENCE: 23

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 24
<211> LENGTH: 152
<212> TYPE: PRT
<213> ORGANISM: Homo sapiens

<400> SEQUENCE: 24

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
                20                  25                  30

Gly Tyr Leu Gln Gly Pro Asn Val Asn Leu Glu Glu Lys Ile Asp Val
            35                  40                  45

Val Pro Ile Glu Pro His Ala Leu Phe Leu Gly Ile His Gly Gly Lys
50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
        130                 135                 140
```

```
Lys Phe Tyr Phe Gln Glu Asp Glu
145                 150

<210> SEQ ID NO 25
<211> LENGTH: 21
<212> TYPE: PRT
<213> ORGANISM: Homo sapiens

<400> SEQUENCE: 25

Met Ala Leu Pro Val Thr Ala Leu Leu Leu Pro Leu Ala Leu Leu Leu
1               5                   10                  15

His Ala Ala Arg Pro
            20

<210> SEQ ID NO 26
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 26

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 27
<211> LENGTH: 45
<212> TYPE: PRT
<213> ORGANISM: Homo sapiens
```

```
<400> SEQUENCE: 27

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 28
<211> LENGTH: 24
<212> TYPE: PRT
<213> ORGANISM: Homo sapiens

<400> SEQUENCE: 28

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 29
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 29

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 30
<211> LENGTH: 112
<212> TYPE: PRT
<213> ORGANISM: Homo sapiens

<400> SEQUENCE: 30

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 31
<211> LENGTH: 80
<212> TYPE: DNA
<213> ORGANISM: Artificial Sequence
```

```
<220> FEATURE:
<223> OTHER INFORMATION: Synthetic polynucleotide

<400> SEQUENCE: 31
guuuuagagc uagaaauagc aaguuaaaau aaggcuaguc cguuaucaac uugaaaaagu    60
ggcaccgagu cggugcuuuu                                                80

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
gcugcagagc cugcugcucu                                                20

<210> SEQ ID NO 33
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 33
gcugcagagc cugcugcucu guuuuagagc uagaaauagc aaguuaaaau aaggcuaguc    60
cguuaucaac uugaaaaagu ggcaccgagu cggugcuuuu                         100

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
ggagcaugug aaugccaucc                                                20

<210> SEQ ID NO 35
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 35
ggagcaugug aaugccaucc guuuuagagc uagaaauagc aaguuaaaau aaggcuaguc    60
cguuaucaac uugaaaaagu ggcaccgagu cggugcuuuu                         100

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
gcaugugaau gccauccagg                                                20

<210> SEQ ID NO 37
<211> LENGTH: 100
<212> TYPE: DNA
<213> ORGANISM: Artificial Sequence
<220> FEATURE:
```

```
<223> OTHER INFORMATION: Synthetic polynucleotide

<400> SEQUENCE: 37
gcaugugaau gccauccagg guuuuagagc uagaaauagc aaguuaaaau aaggcuaguc    60
cguuaucaac uugaaaaagu ggcaccgagu cggugcuuuu                         100

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
gagacgccgg gccuccugga                                               20

<210> SEQ ID NO 39
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 39
gagacgccgg gccuccugga guuuuagagc uagaaauagc aaguuaaaau aaggcuaguc    60
cguuaucaac uugaaaaagu ggcaccgagu cggugcuuuu                         100

<210> SEQ ID NO 40
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 40
gauggcauuc acaugcuccc                                               20

<210> SEQ ID NO 41
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 41
gauggcauuc acaugcuccc guuuuagagc uagaaauagc aaguuaaaau aaggcuaguc    60
cguuaucaac uugaaaaagu ggcaccgagu cggugcuuuu                         100

<210> SEQ ID NO 42
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 42
gcucccaggg cugcgugcug                                               20

<210> SEQ ID NO 43
<211> LENGTH: 100
<212> TYPE: DNA
<213> ORGANISM: Artificial Sequence
<220> FEATURE:
<223> OTHER INFORMATION: Synthetic polynucleotide
```

<400> SEQUENCE: 43
gcucccaggg cugcgugcug guuuuagagc uagaaauagc aaguuaaaau aaggcuaguc    60
cguuaucaac uugaaaaagu ggcaccgagu cggugcuuuu    100

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 44
gcgugcuggg gcugggcgag    20

<210> SEQ ID NO 45
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 45
gcgugcuggg gcugggcgag guuuuagagc uagaaauagc aaguuaaaau aaggcuaguc    60
cguuaucaac uugaaaaagu ggcaccgagu cggugcuuuu    100

<210> SEQ ID NO 46
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 46
gcuggggcug ggcgagcggg    20

<210> SEQ ID NO 47
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 47
gcuggggcug ggcgagcggg guuuuagagc uagaaauagc aaguuaaaau aaggcuaguc    60
cguuaucaac uugaaaaagu ggcaccgagu cggugcuuuu    100

<210> SEQ ID NO 48
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 48
gacuuagugc aaugcaagac    20

<210> SEQ ID NO 49
<211> LENGTH: 100
<212> TYPE: DNA
<213> ORGANISM: Artificial Sequence
<220> FEATURE:
<223> OTHER INFORMATION: Synthetic polynucleotide

```
<400> SEQUENCE: 49
gacuuagugc aaugcaagac guuuuagagc uagaaauagc aaguuaaaau aaggcuaguc    60
cguuaucaac uugaaaaagu ggcaccgagu cggugcuuuu                         100

<210> SEQ ID NO 50
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 50
gauuuacaga ugauuuugaa                                                20

<210> SEQ ID NO 51
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 51
gauuuacaga ugauuuugaa guuuuagagc uagaaauagc aaguuaaaau aaggcuaguc    60
cguuaucaac uugaaaaagu ggcaccgagu cggugcuuuu                         100

<210> SEQ ID NO 52
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 52
aagaaaacac agcuacaac                                                 19

<210> SEQ ID NO 53
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 53
aagaaaacac agcuacaacg uuuuagagcu agaaauagca aguuaaaaua aggcuaguccc   60 guuaucaacu ugaaaaagug gcaccgaguc ggugcuuuu                          99

<210> SEQ ID NO 54
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 54
caacuggagc auuuacugc                                                 19

<210> SEQ ID NO 55
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 55
```

```
caacuggagc auuuacugcg uuuuagagcu agaaauagca aguuaaaaua aggcuaguccc    60 guuaucaacu ugaaaaagug gcaccgaguc ggugcuuuu                            99
```

<210> SEQ ID NO 56
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 56

```
ucuuuguaga acugaagu                                                   19
```

<210> SEQ ID NO 57
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 57

```
ucuuuguaga acugaagug uuuuagagcu agaaauagca aguuaaaaua aggcuaguccc     60 guuaucaacu ugaaaaagug gcaccgaguc ggugcuuuu                            99
```

<210> SEQ ID NO 58
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 58

```
gagcacugaa agcaugaucc                                                 20
```

<210> SEQ ID NO 59
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 59

```
gagcacugaa agcaugaucc guuuuagagc uagaaauagc aaguuaaaau aaggcuaguc     60
cguuaucaac uugaaaaagu ggcaccgagu cggugcuuuu                          100
```

<210> SEQ ID NO 60
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 60

```
ggacguggag cuggccgagg                                                 20
```

<210> SEQ ID NO 61
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 61

```
ggacguggag cuggccgagg guuuuagagc uagaaauagc aaguuaaaau aaggcuaguc    60
cguuaucaac uugaaaaagu ggcaccgagu cggugcuuuu                        100
```

<210> SEQ ID NO 62
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 62

```
gaggcgcucc ccaagaagac                                               20
```

<210> SEQ ID NO 63
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 63

```
gaggcgcucc ccaagaagac guuuuagagc uagaaauagc aaguuaaaau aaggcuaguc    60
cguuaucaac uugaaaaagu ggcaccgagu cggugcuuuu                        100
```

<210> SEQ ID NO 64
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 64

```
gggggcccca gggcuccagg                                               20
```

<210> SEQ ID NO 65
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 65

```
gggggcccca gggcuccagg guuuuagagc uagaaauagc aaguuaaaau aaggcuaguc    60
cguuaucaac uugaaaaagu ggcaccgagu cggugcuuuu                        100
```

<210> SEQ ID NO 66
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 66

```
gcugaggaac aagcaccgcc                                               20
```

<210> SEQ ID NO 67
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 67

```
gcugaggaac aagcaccgcc guuuuagagc uagaaauagc aaguuaaaau aaggcuaguc    60
```

```
cguuaucaac uugaaaaagu ggcaccgagu cgguqcuuuu              100
```

<210> SEQ ID NO 68
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 68

```
ggcgccugcc acgaucagga                                    20
```

<210> SEQ ID NO 69
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 69

```
ggcgccugcc acgaucagga guuuuagagc uagaaauagc aaguuaaaau aaggcuaguc   60
cguuaucaac uugaaaaagu ggcaccgagu cggugcuuuu                       100
```

<210> SEQ ID NO 70
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 70

```
gugcagcagg cagaagagcg                                    20
```

<210> SEQ ID NO 71
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 71

```
gugcagcagg cagaagagcg guuuuagagc uagaaauagc aaguuaaaau aaggcuaguc   60
cguuaucaac uugaaaaagu ggcaccgagu cggugcuuuu                       100
```

<210> SEQ ID NO 72
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 72

```
ggagugaucg gcccccaga                                     19
```

<210> SEQ ID NO 73
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 73

```
ggagugaucg gcccccagag uuuuagagcu agaaauagca aguuaaaaua aggcuaguoc   60
```
guuaucaacu ugaaaaagug gcaccgaguc ggugcuuuu            99

<210> SEQ ID NO 74
<211> LENGTH: 20
<212> TYPE: DNA
<213> ORGANISM: Homo sapiens

<400> SEQUENCE: 74
agagcagcag gctctgcagc                                 20

<210> SEQ ID NO 75
<211> LENGTH: 20
<212> TYPE: DNA
<213> ORGANISM: Homo sapiens

<400> SEQUENCE: 75
ggatggcatt cacatgctcc                                 20

<210> SEQ ID NO 76
<211> LENGTH: 20
<212> TYPE: DNA
<213> ORGANISM: Homo sapiens

<400> SEQUENCE: 76
cctggatggc attcacatgc                                 20

<210> SEQ ID NO 77
<211> LENGTH: 20
<212> TYPE: DNA
<213> ORGANISM: Homo sapiens

<400> SEQUENCE: 77
tccaggaggc ccggcgtctc                                 20

<210> SEQ ID NO 78
<211> LENGTH: 20
<212> TYPE: DNA
<213> ORGANISM: Homo sapiens

<400> SEQUENCE: 78
gggagcatgt gaatgccatc                                 20

<210> SEQ ID NO 79
<211> LENGTH: 20
<212> TYPE: DNA
<213> ORGANISM: Homo sapiens

<400> SEQUENCE: 79
cagcacgcag ccctgggagc                                 20

<210> SEQ ID NO 80
<211> LENGTH: 20
<212> TYPE: DNA
<213> ORGANISM: Homo sapiens

<400> SEQUENCE: 80
ctcgcccagc cccagcacgc                                 20

<210> SEQ ID NO 81
<211> LENGTH: 20
<212> TYPE: DNA
<213> ORGANISM: Homo sapiens

<400> SEQUENCE: 81

```
cccgctcgcc cagccccagc                                                  20

<210> SEQ ID NO 82
<211> LENGTH: 20
<212> TYPE: DNA
<213> ORGANISM: Homo sapiens

<400> SEQUENCE: 82
gtcttgcatt gcactaagtc                                                  20

<210> SEQ ID NO 83
<211> LENGTH: 20
<212> TYPE: DNA
<213> ORGANISM: Homo sapiens

<400> SEQUENCE: 83
ttcaaaatca tctgtaaatc                                                  20

<210> SEQ ID NO 84
<211> LENGTH: 19
<212> TYPE: DNA
<213> ORGANISM: Homo sapiens

<400> SEQUENCE: 84
gttgtagctg tgttttctt                                                   19

<210> SEQ ID NO 85
<211> LENGTH: 19
<212> TYPE: DNA
<213> ORGANISM: Homo sapiens

<400> SEQUENCE: 85
gcagtaaatg ctccagttg                                                   19

<210> SEQ ID NO 86
<211> LENGTH: 19
<212> TYPE: DNA
<213> ORGANISM: Homo sapiens

<400> SEQUENCE: 86
acttcaagtt ctacaaaga                                                   19

<210> SEQ ID NO 87
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 87
ggatcatgct ttcagtgctc                                                  20

<210> SEQ ID NO 88
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 88
cctcggccag ctccacgtcc                                                  20

<210> SEQ ID NO 89
```

```
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 89
gtcttcttgg ggagcgcctc                                              20

<210> SEQ ID NO 90
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 90
cctggagccc tggggccccc                                              20

<210> SEQ ID NO 91
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 91
ggcggtgctt gttcctcagc                                              20

<210> SEQ ID NO 92
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 92
tcctgatcgt ggcaggcgcc                                              20

<210> SEQ ID NO 93
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 93
cgctcttctg cctgctgcac                                              20

<210> SEQ ID NO 94
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 94
tctgggggcc gatcactcc                                               19
```

MODIFICATION OF IMMUNE CELLS FOR REDUCING TOXICITY AND USES THEREOF IN ADOPTIVE CELL THERAPY

RELATED APPLICATIONS

The present application is a United States National Phase under 35 U.S.C. § 371 of International Application No. PCT/US2019/022093, filed on Mar. 13, 2019, which claims the benefit of the filing date under 35 U.S. C. § 119 of U.S. Provisional Application Ser. No. 62/642,821, filed Mar. 14, 2018, the entire contents of each of which are incorporated by reference herein.

SEQUENCE LISTING

The instant application contains a Sequence Listing which has been filed electronically in ASCII format and is hereby incorporated by reference in its entirety. Said ASCII copy, created on Sep. 11, 2020, is named 112126-0024-70000US01_SeqenceLst.txt and is 25,635 bytes in size.

BACKGROUND OF THE INVENTION

Adoptive cell transfer therapy is a type of immunotherapy that involves ex vivo expansion of autologous or allogenic immune cells and subsequent infusion into a patient. The immune cells may be modified ex vivo to specifically target malignant cells. The promise of adoptive cell transfer therapy is often limited by toxicity (e.g., cytokine-associated toxicity). For example, adoptive cell transfer immunotherapy may trigger non-physiologic elevation of cytokine levels (cytokine release syndrome), which could lead to death of recipients (see, e.g., Morgan et al., *Molecular Therapy* 18(4): 843-851, 2010).

It is therefore of great interest to develop approaches to reduce toxicity associated with adoptive cell transfer immunotherapy, while maintaining efficacy.

SUMMARY OF THE INVENTION

The present disclosure is based, at least in part, on the development of approaches to reduce inflammatory properties of immune cells for use in adoptive cell therapy and toxicity associated with adoptive immune cell therapy. Such approaches may comprise knock-out of endogenous genes coding for inflammatory proteins, knock-in antagonists of such inflammatory proteins and immune suppressive cytokines, or a combination thereof. Accordingly, one aspect of the present disclosure features a population of immune cells, comprising: (i) a first plurality of modified immune cells, which produces a reduced level of one or more inflammatory proteins as compared with wild-type immune cells of the same type under the same conditions; and (ii) a second plurality of modified immune cells, which expresses an antagonist(s) of the one or more inflammatory proteins and/or express one or more immune suppressive cytokines. In some embodiments, at least one endogenous allele of the one or more inflammatory proteins is knocked out in each cell of the first plurality of the modified immune cells. In some embodiments, the first plurality of modified immune cells, the second plurality of modified immune cells, or both, are T cells or natural killer cells.

In some embodiments, the inflammatory proteins comprise one or more inflammatory cytokines or soluble receptors thereof, one or more inflammatory growth factors, one or more cytotoxic molecules, or a combination thereof. Exemplary inflammatory cytokines or soluble receptors thereof include, but are not limited to, IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, and VWF. Exemplary inflammatory growth factors include, but are not limited to, TGFα, VEGF, EGF, HGF, and FGF. Exemplary cytotoxic molecules include, but are not limited to, perforin, granzyme, and ferritin.

In some embodiments, the second plurality of modified immune cells comprises an exogenous nucleic acid(s) coding for the antagonist(s) of one or more inflammatory proteins and/or one or more immune suppressive cytokines. At least one of the exogenous nucleic acid may be incorporated into the genome of the first plurality of modified immune cells.

In some embodiments, the one or more antagonists of the one or more inflammatory proteins introduced into any of the second plurality of modified immune cells comprise a soluble receptor of the inflammatory protein and/or an antibody specific to the inflammatory protein.

In other embodiments, an immune suppressive cytokine is introduced into the second plurality of modified immune cells. Exemplary immune suppressive cytokines include, but are not limited to, TGFβ, IL-4, IL-10, IL-13, IL-33, IL-35, and IL-37.

In some embodiments, the first plurality of modified immune cells and the second plurality of immune cells of any of the immune cell populations described herein can be of the same type. Alternatively or in addition, the first plurality of modified immune cells overlaps with the second plurality of immune cells.

In another aspect, the present disclosure provides a population of immune cells, comprising a first plurality of modified immune cells, which produces less interleukin 2 (IL-2) as relative to wild-type immune cells of the same type under the same conditions. For example, at least one endogenous IL-2 allele is knocked out in each cell of the first plurality of the modified immune cells. In some instances, the first plurality of modified immune cells, when activated, produces less IL-2 as relative to the wildtype immune cells activated under the same conditions.

In other instances, the total IL-2 production by the population of immune cells is about 30-95% less than a wild-type counterpart under the same conditions. For example, the total IL-2 production by the population of immune cells is about 50% of that by the wild-type counterpart.

In some embodiments, the population of immune cells described above may further comprise a second plurality of modified immune cells, which produces a reduced level of one or more of inflammatory proteins as described herein, when compared with wildtype immune cells of the same type. For example, the total level of the one or more inflammatory protein produced by the population of immune cells is at least 10% lower than that of a wild-type counterpart under the same conditions. In some examples, at least one endogenous allele of the one or more inflammatory protein is knocked out in each cell of the second plurality of the modified immune cells.

In some embodiments, the first plurality of modified immune cells and the second plurality of modified immune cells are of the same type. In other embodiments, the first plurality of modified immune cells and the second plurality of modified immune cells are overlapping.

Alternatively or in addition, the population of immune cells described above may further comprise a third plurality of modified immune cells, which expresses one or more exogenous antagonists of the one or more inflammatory proteins or one or more immune suppressive cytokines as described herein. In some particular examples, the one or more inflammatory proteins comprise IL6 and the antagonist of IL6 is tocilizumab or sirukumab, or an antigen-binding fragment thereof (e.g., a single-chain antibody fragment (scFv) derived from tocilizumab or sirukumab).

The third plurality of modified immune cells may comprise one or more exogenous nucleic acids coding for the one or more antagonists of the one or more cytokines. At least one of the exogenous nucleic acid may be incorporated into the genome of the third plurality of modified immune cells. In some examples, the third plurality of modified immune cells are of the same type as the first plurality of modified immune cells, the second plurality of modified immune cells, or both. In other examples, the third plurality of modified immune cells overlaps with the first plurality of modified immune cells, the second plurality of modified immune cells, or both.

In any or the immune cell populations described herein, the immune cells can be T-cells, NK cells, dendritic cells, macrophages, B cells, neutrophils, eosinophils, basophils, mast cells, myeloid-derived suppressor cells, mesenchymal stem cells, precursors thereof, or a combination thereof. In some embodiments, the immune cells may be further modified to express a chimeric antigen receptor (CAR) and/or an exogenous T cell receptor. The CAR may comprise an extracellular ligand binding domain, a transmembrane domain, and one or more intracellular signaling domains. In some examples, the extracellular ligand binding domain may comprise a single-chain antibody fragment specific to a cell surface protein, an extracellular domain of a cytokine receptor, or an extracellular domain of a co-stimulatory receptor. Alternatively or in addition, the one or more one or more intracellular signaling domains may comprise (i) a signaling domain of CD3ζ, and (ii) one or more signaling domains from one or more co-stimulatory proteins or cytokine receptors. In other examples, the CAR may comprise one or more stimulatory domains (e.g., co-stimulatory domains) from CD28, 4-1BB, 2B4, KIR, CD27, OX40, ICOS, MYD88, IL2 receptor, and/or SynNotch.

In yet another embodiment, the present disclosure provides a method of producing a population of modified immune cells with reduced inflammatory properties, the method comprising: (i) providing a population of immune cells; and (ii) modifying the immune cells to reduce IL-2 production thereby. Such a method may further comprise (iii) modifying the immune cells to the production of one or more inflammatory proteins as described herein, and optionally (iv) introducing into the immune cells one or more nucleic acids coding for one or more antagonists of one or more inflammatory proteins and/or one or more immune suppressive cytokines as also described herein, wherein the one or more nucleic acids are in operably linkage to a promoter(s) for expression of the one or more antagonists in the immune cells.

Alternatively, provided herein is a method of producing a population of modified immune cells with reduced inflammatory properties, the method comprising: (i) providing a population of immune cells; (ii) modifying the immune cells to reduce production of one or more of inflammatory proteins as described herein; and (iii) introducing into the immune cells one or more nucleic acids coding for one or more antagonists of one or more inflammatory proteins and/or one or more immune suppressive cytokines as also described herein, wherein the one or more nucleic acids are in operably linkage to a promoter(s) for expression of the one or more antagonists in the immune cells.

In any of the methods described herein, the modifying step comprises gene editing at an endogenous allele of a target protein (e.g., IL-2 or an inflammatory protein) of the immune cells. The gene editing may comprise Clustered Regularly Interspaced Short Palindromic Repeats (CRISPR), Transcription activator-like effector nuclease (TALEN), or Zinc finger nuclease (ZFN), an endonuclease, a meganuclease, mega-TALS, or a combination thereof. In some instances, the IL-2 production may be reduced by about 30-95% (e.g., about 50%) via gene.

In any of the methods described herein, the immune cells can be T-cells, NK cells, dendritic cells, macrophages, B cells, neutrophils, eosinophils, basophils, mast cells, myeloid-derived suppressor cells, precursors thereof, or a combination thereof. Any of the immune cells may further express a chimeric antigen receptor (CAR) and/or an exogenous T cell receptor, which are also described herein.

Any of the immune cell populations prepared by a method described herein is also within the scope of the present disclosure.

Further, provided herein is a method of cell therapy, comprising administering to a subject in need thereof a population of any of the immune cells described herein. The subject may be a human patient having a target disease as described herein, for example, cancer, an infectious disease, or an immune disorder.

Also within the scope of the present disclosure are immune cell populations as described herein for use in treating the target disease as also described herein, and uses of such immune cell population in manufacturing a medicament for use in treatment of a target disease.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1:
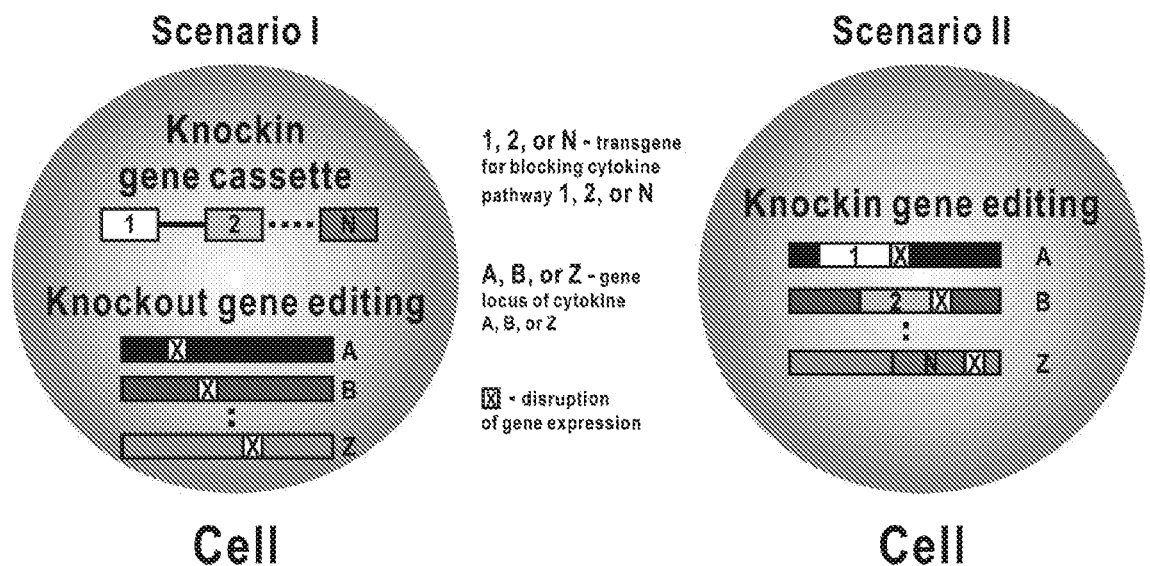
FIG. 1 includes schematic representations of exemplary scenarios using gene editing to neutralize inflammatory cytokine pathways. The left panel shows a combination of knock-in gene cassettes and knockout gene editing (scenario I). The right panel depicts an equivalent one-step strategy to scenario I by integrating transgene knock-in and gene disruption at the same time (scenario II).

Adoptive cell transfer immunotherapy relies on immune cell activation and cytokine secretion to eliminate disease cells. However, systemic overproduction of cytokines raises safety concerns and sometimes can be fatal to the recipients. Morgan et al., *Molecular Therapy* 18(4):843-851, 2010. The present disclosure aims to overcome this limitation, in part, via the development of immune cells having reduced inflammatory properties. As described herein, this can be achieved by knocking out one or more cytokines or receptors thereof in the immune cells to reduce undesired cytokines (e.g., inflammatory cytokines) produced by the immune cells to be transplanted to a recipient upon activation and/or by knocking in one or more cytokine antagonists to the immune cells, which can neutralize inflammatory signaling mediated by cytokines produced by host immune cells of the recipient upon activation by the immune cells administered to the recipient. The combination of knocking-in and knocking-out designs would reduce production and/or signaling of undesired cytokines (e.g., inflammatory cytokines) by both the immune cells for use in adoptive therapy and host immune cells, thereby significantly reduce toxicity caused by immune cell adoptive therapy due to cytokine crisis.

In some examples, interleukin 2 (IL-2) may be knocked out in immune cells for use in adoptive immune cell therapy. IL-2 has been characterized as a T-cell mitogen essential for T cell proliferation/activation. See, e.g., Morgan et al., *Science*, 193(4257):1007-8, 1976; Smith, *Science*, 240 (4856):1169-76, 1988). Surprisingly, studies described herein showed that reduction of IL2 production in immune cells (e.g., T cells) inhibits cell over-proliferation while maintains a healthy propagation rate for these immune cells in vitro. These results indicate that IL-2 can be a target cytokine for knocking-out to reduce toxicity associated with adoptive cell therapy.

The modified immune cells as described herein, comprising knock-out of one or more inflammatory proteins (e.g., inflammatory cytokines or soluble receptors thereof, inflammatory growth factors, or cytotoxic molecules), knock-in of one or more antagonists of the inflammatory proteins or immune suppressive cytokines, or a combination thereof, would be beneficial in limiting cytokine-associated toxicity in adoptive cell transfer immunotherapy and would be useful in treating diseases, including cancer, infectious diseases and immune disorders effectively with less side effects.

Accordingly, provided herein are populations of immune cells comprising modified immune cells having reduced inflammatory properties as described herein, methods of producing such cell populations and uses thereof for decreasing inflammation associated with immune cell adoptive therapy.

I. Modified Immune Cells

One aspect of the present disclosure provides modified immune cells having reduced inflammatory properties compared to wild-type immune cells of the same type. Such modified immune cells may comprise knock-out of one or more inflammatory proteins (e.g., inflammatory cytokines or soluble receptors thereof, inflammatory growth factors, or cytotoxic molecules), knock-in of one or more antagonists of the inflammatory proteins or immune suppressive cytokines, or a combination thereof. Wild-type cells refer to those that have no such knock-in and knock-out modifications.

(i) Inflammatory Proteins and Immune Suppressive Cytokines

As used herein, inflammatory proteins refer to proteins that are capable of promoting inflammation, either directly or indirectly. An inflammatory protein may be an inflammatory cytokine or a soluble receptor of the inflammatory cytokine, inflammatory growth factors, or a cytotoxic molecule.

In some embodiments, the inflammatory protein is an inflammatory cytokine or a soluble receptor of the inflammatory cytokine, which promotes inflammation. In some instances, such inflammation cytokines are produced by and involved in the upregulation of inflammatory reactions. In nature, inflammatory cytokines are typically secreted by immune cells such as helper T cells, macrophages, or certain other types of immune cells.

Exemplary inflammatory cytokines or a soluble receptor thereof include interleukin 1 alpha (IL1α), interleukin 1 beta (IL1β), interleukin 2 (IL-2), interleukin 5 (IL-5), interleukin 6 (IL-6), interleukin 7 (IL-7), interleukin 8 (IL-8), interleukin 9 (IL-9), interleukin (IL-12), interleukin 15 (IL-15), interleukin 17 (IL-17), interleukin 18 (IL-18), interleukin 21 (IL-21), interleukin 23 (IL-23), sIL-1RI, sIL-2Rα, soluble IL-6 receptor (sIL6R), interferon α (IFNα), interferon β (IFNβ), interferon γ (IFNγ), Macrophage inflammatory proteins (e.g., MIPα and MIPβ), Macrophage colony-stimulating factor 1 (CSF1), leukemia inhibitory factor (LIF), granulocyte colony-stimulating factor (G-CSF), granulocyte-macrophage colony-stimulating factor (GM-CSF), C-X-C motif chemokine ligand 10 (CXCL10), chemokine (C-C motif) ligand 5 (CCL5), eotaxin, tumor necrosis factor (TNF), monocyte chemoattractant protein 1 (MCP1), monokine induced by gamma interferon (MIG), receptor for advanced glycation end-products (RAGE), c-reactive protein (CRP), angiopoietin-2, and von Willebrand factor (VWF).

IL1α is also referred to as hematopoietin 1 and is a member of the interleukin 1 family of cytokines. This cytokine is produced by activated macrophages, epithelial cells, endothelial cell and macrophages and signals through the interleukin-1 receptor. Human IL1α (e.g., GenBank Accession No. NP_000566.3) is encoded by the IL1A gene.

IL1β is a member of the interleukin 1 family of cytokines and signals through the ILB receptor. IL1β has been implicated in promoting inflammation in various diseases including type 1 diabetes and rheumatoid arthritis. For example, IL11 signaling is capable of promoting inflammatory pain hypersensitivity by inducing cyclooxygenase-2 (PTGS2/COX2) expression. Human IL1β (e.g., GenBank Accession No. NP_000567.1) is encoded by the IL1B gene.

The interleukin 1 type I receptor (a.k.a., IL-1RI is encoded by the IL1R1 gene in humans. sIL-1RI refers to a soluble form of the IL-1RI receptor. Exemplary human IL-1RI sequences are provided under GenBank Accession NP_001307910.1, NP_001275635.1, NP_001307912.1, NP_001307913.1, NP_001307914.1 and NP_001307915.1.

IL-2 is a member of the IL-2 family of cytokines and plays a key role in stimulating lymphocyte proliferation (e.g., T cells and B cells) (see, e.g., Morgan et al., *Science*, 193(4257):1007-8, 1976; Smith, *Science*, 240(4856):1169-76, 1988; and Mingari et al., *Nature*, 312(5995):641-3, 1984). IL-2 is mainly produced by T cells (e.g., CD4+ and CD8+ T cells) following T cell activation by an antigen, and has also been reported to be expressed by dendritic cells and mast cells (see, e.g., Granucci et al., *Nature Immunol.*, 2(9):882-8, 2001; and Hershko et al., *Immunity*, 35(4):562-71, 2011). By binding a high-affinity trimeric or low-affinity dimeric IL-2 receptor (IL-2R) complex, IL-2 can act on numerous cell types to trigger immune responses. Taniguchi et al., *Cell*, 73(1):5-8, 1993. CD122 and CD132 form a dimeric receptor for IL-2 (IL-2R), while trimeric IL-2R also includes CD25. Human IL-2 (e.g., GenBank Accession No.: NP_000577.2) is encoded by the IL-2 gene.

Soluble IL2 receptor a subunit (sIL2Ra) is a soluble form of CD25. sIL2Ra is often secreted by activated T cells and B cells (see, e.g., Rubin et al., *J Immunol.*, 135(5):3172-7, 1985). Elevated sIL2Ra levels have been associated with hematologic malignancies and autoimmune disorders (see, e.g., Rubin et al., *Ann Intern Med.*, 113(8):619-27, 1990). In one example, sIL2Ra is human sIL2Ra.

IL-5 is a member of a discrete cytokine family that also includes granulocyte-macrophage colony-stimulating factor (GM-CSF) and interleukin-3. IL-5 signals through the interleukin-5 receptor and can stimulate B cell growth. An exemplary human IL-5 sequence is provided at GenBank Accession No. NP_000870.1.

IL-6 is a pleiotropic cytokine that is often produced by antigen presenting cells (including dendritic cells), macrophages and B cells in response to tissue injuries and infections and has additional roles in regulating cell growth and differentiation (see, e.g., Kamimura et al., *Rev Physiol Biochem Pharmacol.* 149:1-38, 2003). IL6 is implicated in inducing B-cell differentiation, promoting acute phase protein synthesis in hepatocytes, enhancing growth of plasma cell and myeloma fusion cells and in possessing interferon antiviral activity. Given IL6's various functions, IL6 is also referred to as B-cell stimulatory factor 2 (BSF2), hepatocyte-stimulating factor (HSF), hybridoma growth factor (HGF) and IFN-02 (Kishimoto, Blood. 74(1):1-10, 1989). As an example, the amino acid sequence of human IL6 is provided under GenBank Accession No. NP_000591.1.

IL-6 signals through a complex comprising the membrane glycoprotein gp130 and the IL-6 receptor (IL6R) (see, e.g., Hibi et al., *Cell*, 63(6):1149-57, 1990). IL-6 binding to IL6R on target cells promotes gp130 homodimerization and subsequent signal transduction. As used herein, IL6R includes both membrane bound and soluble forms of IL6R (sIL6R). When bound to IL-6, soluble IL6R (sIL6R) acts as an agonist and can also promote gp130 dimerization and signaling. Transsignaling can occur whereby sIL-6R secretion by a particular cell type induces cells that only express gp130 to respond to IL-6 (see, e.g., Taga et al., *Annu Rev Immunol.*, 15:797-819, 1997; and Rose-John et al., *Biochem J.*, 300 (Pt 2):281-90, 1994). In one example, sIL6R comprises the extracellular domain of human IL6R (see e.g., Peters et al., *J Exp Med.*, 183(4):1399-406, 1996).

IL-7 is a cytokine implicated in development of B and T cells. IL7 can function as a pre-pro-B cell growth-stimulating factor by forming a heterodimer with hepatocyte growth factor. Exemplary human IL-7 sequences are provided at GenBank Accession Numbers NP_000871.1, NP_001186815.1, NP_001186816.1 and NP_001186817.1.

IL-8 is a chemoattractant cytokine and is secreted by a variety of cell types including leukocytes, monocytes and endothelial cells (see, e.g., Baggiolini et al., *J. Clin. Invest.* 84:1045-1049, 1989). Although the primary target cells of IL-8 are neutrophils, IL-8 has also been reported to function as a chemotactic factor for other cell types, including basophils and T cells. IL-8 can signal through two G-protein coupled receptors, CXCR1 and CXCR2 in humans (see, e.g., Wu et al., *Science*. 261(5117):101-3, 1993; and Damaj et al., *J. Biol. Chem.*, 271(22):12783-9, 1996). As an example, the CXCL8 gene in humans encodes at least two IL-8 isoforms. Human IL-8 isoform 1 is longer in length than isoform 2 and is generally expressed in nonimmune cells, while isoform 2 is mainly expressed in monocytes and macrophages. An exemplary human IL-8 isoform 2 is provided at Genbank Accession No. NP_001341769.1.

IL-9 is a cytokine that is implicated as regulator of hematopoietic cells and can stimulate cell proliferation. IL-9 signals through the interleukin 9 receptor and can activate signal transducer and activator (STAT) proteins. An exemplary human IL-9 sequence is provided at GenBank Accession No. NP_000581.1.

IL-12 is a member of the interleukin 12 family of cytokines, which includes IL-12, IL-23, IL-27 and IL-35. In response to antigen, IL-12 can be produced by neutrophils, dendritic cells and macrophages. IL12 predominantly acts on naïve CD4+ T cells. This cytokine is made of two subunits. As a heterodimer, IL-12 is composed of IL-12 subunit alpha (IL-12 p35) and IL-12 subunit beta (IL-12 p40). In humans, each subunit is encoded by a different gene. For example, human IL-12 subunit alpha (e.g., GenBank Accession Numbers NP_000873.2, NP_001341511.1 and NP_001341512.1) is encoded by the IL12A gene, while human IL-12 subunit beta (e.g., GenBank Accession Number NP_002178.2) is encoded by the IL12B gene.

IL-15 is a member of the 4-alpha-helix bundle family of cytokines and has been implicated promoting differentiation and proliferation of B cells, T cells and natural killer cells (see, e.g., Mishra et al., *Clin Cancer Res.*, 20(8):2044-50, 2014). IL-15 can act on antigen-presenting dendritic cells, macrophages and monocytes by binding a heterotrimeric IL-15 receptor complex. The IL-15 receptor complex has three subunits, including IL15Rα, IL-2Rβ and IL-2Rγ (see, e.g., Mishra et al., *Clin Cancer Res.*, 20(8):2044-50, 2014). The IL15Ra subunit has a high affinity for IL-15 and exists in a soluble and membrane form. As an example, the amino acid sequence of human IL-15 is provided in GenBank Accession No. NP_751915.1.

Interleukin 17 (a.k.a., IL17A, CTLA8 or IL-17) is a member of the IL17 family of cytokines, Gu et al., *Cytokine*, 64(2):477-85, 2013. IL-17 is predominantly produced by T helper 17 cells (Th17 cells). By signaling through a heterodimeric receptor complex of IL17RA/IL17RC, IL-17 can induce stromal cells to express inflammatory cytokines and chemokines (see, e.g., Toy et al., *J Immunol.*, 177(1):36-9, 2006). As an example, the human IL17A gene encodes IL-17 (e.g., Genbank Accession No. NP_002181.1).

IL-18 is a member of the interleukin 1 superfamily of cytokines. IL-18 is produced by various cells including macrophages and signals through the interleukin-18 receptor. Exemplary human IL-18 sequences are provided at GenBank Accession Numbers NP_001553.1 and NP_001230140.1.

IL-21 is a member of the common-gamma chain family of cytokines, which include IL-2, IL-4, IL-7, IL-9, IL-15, and IL-21. IL-21 is produced by activated CD4+ T cells and can act on T cells, B cells and natural killer cells by interacting with the IL-21 receptor. Exemplary human IL-21 sequences are provided at GenBank Accession Numbers NP_068575.1 and NP_001193935.1.

IL-23 is a heterodimeric cytokine composed of an IL12 beta subunit (IL-12p40) subunit and the IL23A (IL-23p19) subunit. IL-23 signals through the IL23 receptor, which is made of beta 1 subunit of IL12 (IL12RB1) and an IL23 specific subunit, IL23R. Similar to IL-12, IL-23 can engage STAT4 signaling but IL23 predominantly acts on memory CD4+ T cells. An exemplary human IL-23A sequence is provided under GenBank Accession No. NP_057668.1.

Interferons (IFNs) are a family of cytokines that are implicated in innate immunity and defense against viral infection in host cells. There are at least two types of interferons (see, e.g., Le Page et al., *Rev. Immunogenet.*, 2(3):374-86, 2000). Type I interferons (including IFNα and IFNβ) are generally produced by virus-infected cells. In contrast, type II interferons (e.g., IFNγ) are generally produced by macrophages, T cells and natural killer cells (NK). For example, the human genes IFNA1, IFNB1, and IFNG encode IFNα (e.g., Genbank Accession No. NP_076918.1), IFNβ (e.g., Genbank Accession No. NP_002167.1), and IFNγ (e.g., Genbank Accession No. NP_000610.2), respectively.

Macrophage inflammatory proteins (MIPs or also referred to as MIP-1 CC proteins) are chemotactic cytokines and there are at least four members of this subfamily. Members of the MIP family include CCL3 (MIP-1α), CCL4 (MIP-1β), CCL9 (MIP-1δ or also previously designated as CCL10), and CCL15 (MIP-1γ) (see, e.g., Maurer et al., *Int J Biochem Cell Biol.*, 36(10):1882-6, 2004). These proteins may be produced by different cell types including macrophages, dendritic cells and lymphocytes (Driscoll, *Exp Lung Res.*, 20(6):473-90, 1994). MIPs signal through G-protein-coupled cell surface receptors, which include CCR1, CCR3 and CCR5. These receptors are often expressed by monocytes/macrophages and lymphocytes. Exemplary MIPs include, but are not limited to, human CCL3 (MIP-1α) (e.g., Genbank Accession No. NP_002974.1), human CCL4 (MIP-1β) (e.g., Genbank Accession No. NP_002975.1) and human CCL15 (MIP-1γ) (e.g., Genbank Accession No. NP_116741.2).

CSF1 (a.k.a. macrophage colony-stimulating factor or M-CSF) is a cytokine involved in differentiation of hematopoietic stem cells into macrophages. CSF1 binds to the colony stimulating factor 1 receptor. Exemplary human CSF1 sequences are provided under GenBank Accession Numbers AAA52117.1, NP_000748.3, NP_757349.1 and NP_757350.1.

LIF is a pleiotropic cytokine that is implicated in hematopoietic differentiation in myeloid and normal leukemia cells, in neuronal cell differentiation and in kidney development. LIF acts on the LIF receptor (LIFR-α). Exemplary LIF sequences are provided under GenBank Accession Numbers NP_002300.1 and NP_001244064.1.

G-CSF is a cytokine involved in the production, function and differentiation of granulocytes. G-CSF Is produced by a variety of cells including endothelial cells and macrophages. G-CSF binds to the G-CSF receptor. Exemplary G-CSF sequences are provided under GenBank Accession Numbers NP_000750.1, NP_757373.1, NP_757374.2 and NP_001171618.1.

Granulocyte-macrophage colony-stimulating factor (GM-CSF) is a member of the colony-stimulating factor superfamily and is expressed by many different immune cells including macrophages, mast cells, natural killer cells and T cells. As a cytokine, GM-CSF can function as a hematopoietic growth factor (Metcalf, *Nature*, 339(6219):27-30, 1989). GM-CSF can promote the growth and differentiation of various hematopoietic precursor cells including granulocytes, eosinophils, erythrocytes and macrophages by activating the GM-CSF receptor (GM-CSFR) (see, e.g., Martinez-Moczygemba et al., *J Allergy Clin Immunol.* 112(4): 653-65, 2003). As an example, human GM-CSF (e.g., GenBank Accession No.: NP_000749.2) is encoded by the CSF2 gene.

CXCL10 (a.k.a. interferon γ-induced protein 10 or IP-10) is a cytokine that is secreted by various cell types (e.g., fibroblasts, endothelial cells and monocytes) in response to interferon γ. CXCL10 has been implicated in chemoattraction and T cell adhesion to endothelial cells and acts on the chemokine receptor CXCR3. An exemplary human CXCL10 sequence is provided under GenBank Accession No. NP_001556.2.

CCL5 (a.k.a. D17S136E, RANTES, SCYA5, SIS-delta, SISd, TCP228, eoCP or C-C motif chemokine ligand 5) is a chemoattractant for blood monocytes, memory T helper cells and eosinophils. CCL5 can bind the chemokine receptor CCR5. Exemplary human CCL5 sequences are provided under GenBank Accession numbers NP_002976.2 and NP_001265665.1.

Eotaxins form a CC chemokine subfamily of eosinophil chemotactic proteins. Members of this family include CCL11 (eotaxin-1), CCL24 (eotaxin-2) and CCL26 (eotaxin-3). Exemplary human eotaxins are provided under GenBank Accession Numbers CCL11 (NP_002977.1), (NP_002977.1), CCL24 (NP_002982.2), and CCL26 (NP_006063.1).

Tumor necrosis factor (TNF, e.g., TNFα) is a member of the tumor necrosis factor superfamily of cytokines. TNF is primarily secreted by macrophages and activated T cells and can signal through two different receptors (TNFR1 and TNFR2) to regulate various cellular functions, including apoptosis, cell survival and differentiation (Liu, *Cell Res.*, 15(1):24-7, 2005). As an example, human TNFα (e.g., Genbank Accession No.: NP_000585.2) is encoded by the TNF gene.

Monocyte chemotactic protein 1 (MCP1 or CCL2) is a member of the chemokine family of cytokines. MCP1 can function as a chemoattractant and signals through the G-protein-coupled receptor CCR2 to recruit dendritic cells, memory T cells and monocytes following an infection or injury (see, e.g., Deshmane et al., *J Interferon Cytokine Res.*, 29(6):313-26, 2009). In one example, the MCP1 is human MCP1 (e.g., GenBank Accession No. NP_002973.1).

MIG (a.k.a. CXCL9, CMK, Humig, MIG, SCYB9, crg-10 or C-X-C motif chemokine ligand 9) is a member of the CXC chemokine family. MIG is a chemoattractant for T-cells and its expression is upregulated by IFN γ. An exemplary human MIG sequence is provided under GenBank Accession No. NP_002407.1.

Advanced glycosylation end product receptor (RAGE or AGER) belongs to the immunoglobulin superfamily of cell surface receptors. RAGE can bind multiple ligands including advanced glycosylation end product and is implicated in innate immunity. Exemplary human RAGE proteins are provided under GenBank Accession Numbers NP_001127.1, NP_001193858.1, NP_001193861.1, NP_001193863.1, NP_001193865.1, NP_001193869.1, NP_751947.1 and NP_001193883.1.

C-reactive protein (CRP) is a member of the pentraxin family, which also includes serum amyloid P component (SAP). Circulating levels of the acute-phase protein CRP are often elevated in response to tissue injury, infection and inflammation. There are a variety of CRP ligands, but CRP has the highest affinity for phosphocholine-containing ligands, which are often found on the surface of necrotic and apoptotic cells. CRP-binding to lysophospholipids on the surface of damaged and apoptotic cells recruits C1q and subsequent activation of the complement system (see, e.g., Thompson et al., *Structure*. February 15; 7(2):169-77, 1999; Pepys et al., *J Clin Invest*. 111(12): 1805-1812, 2003). As an example, the amino acid sequence of human CRP can be found under GenBank Accession No. NP_000558.2.

Angiopoietin-2 (Ang2) is a member of the angiopoietin family, which include angiopoietin-1, angiopoietin-2 and angiopoietin-4. Ang2 has been implicated in regulation of endothelial cell junctions, destabilization of blood vessels and increased vascular permeability (see, e.g., Zheng et al., *Genes Dev.,* 28(14):1592-603, 2014; and Ziegler et al., *J Clin Invest*. pii: 66549, 2013). As a Tie2 receptor ligand, Ang2 can also modulate vascular remodeling through regulation of Tie2 signaling (see, e.g., Thurston et al., *Cold Spring Harb Perspect Med.,* 2(9):a006550, 2012). As an example, the amino acid sequence of human Ang2 can be found under GenBank Accession No. NP_001138.1.

Von Willebrand factor (VMF) is a glycoprotein involved in regulation of hemostasis. This protein is often present in blood plasma, subendothelial connective tissue and platelet α-grandules. To mediate hemostasis, VWF can promote platelet adhesion to subendothelial connective tissue and also bind factor VIII, which is a blood clotting factor (Sadler, *Annu Rev Biochem.* 67:395-424, 1998). VWF deficiency causes von Willebrand disease, which is a hereditary bleeding disorder. As an example, the amino acid sequence of human VMF can be found under GenBank Accession No. NP_000543.2.

In some embodiments, an inflammatory protein is an inflammatory growth factor. As used herein, inflammatory growth factors are growth factors that play some roles (directly or indirectly) in inflammatory signaling pathways. In some instances, an inflammatory growth factor may interplay with one or cytokines to promote inflammation. Exemplary inflammatory growth factors include transforming growth factor α (TGFα), vascular endothelial factor (VEGF), epidermal growth factor (EGF), hepatocyte growth factor (HGF), and fibroblast growth factor (FGF).

TGFα is a growth factor implicated in cell proliferation, cell development and differentiation. It can signal through the epidermal growth factor receptor (EGFR). Exemplary human TGFα sequences are provided under GenBank Accession Numbers NP_003227.1, NP_001093161.1, NP_001295087.1 and NP_001295088.1.

VEGF (a.k.a. vascular permeability factor or VPF) is a family of proteins involved in blood vessel formation. In mammals, there are at least five VEGF family members including VEGF-A, placenta growth factor (PGF), VEGF-B, VEGF-C and VEGF-D. An exemplary human VEGF sequence is provided at GenBank Accession Number NP_001165097.1.

EGF is a growth factor that promotes cell growth, survival and differentiation. EGF is a ligand for the receptor, EGFR. Exemplary human EGF sequences are provided at GenBank Accession Numbers NP_001954.2, NP_001171601.1, NP_001171602.1 and NP_001343950.1.

HGF is a growth factor implicated in regulation of cell motility, cell growth and morphogenesis. HGF binds to the c-MET receptor and is produced by mesenchymal cells. Exemplary human HGF sequences are provided at GenBank Accession Numbers NP_000592.3, NP_001010931.1, NP_001010932.1, NP_001010933.1 and NP_001010934.1.

FGF is a family of signaling molecules implicated in a variety of processes, including development. In humans, there are at least 22 members of the FGF family. For example, human FGF1, FGF2, FGF3, FGF4, FGF5, FGF6, FGF7, FGF8, FGF9 and FGF10 bind to FGF receptors. Exemplary humans FGFs are provided under GenBank Accession Numbers NP_000791.1, NP_001997.5 and NP_005238.1.

In some embodiments, an inflammatory protein is a cytotoxic molecule. As used herein, cytotoxic molecules are molecules secreted by immune cells such as macrophages to kill disease cells. Exemplary cytotoxic molecules include perforin, granzyme, and ferritin.

Perforin is a cytolytic protein localized to the granules of cytotoxic T lymphocytes and natural killer cells. Upon secretion of cytolytic granules, perforin engages with the membrane of target cells and forms pores in the plasma membrane (see, e.g., Liu et al., *J Immunol.* 156(9):3292-300, 1996). In humans, perforin (e.g., Genbank Accession No. NP_001076585.1) is encoded by the PRF1 gene.

Granzymes are serine proteases that are secreted by cytotoxic T cell and natural killer cell granules and are implicated in inducing apoptosis in target cells (e.g., cells that have been infected with a pathogen or have become malignant). In humans, there are at least five types of granzymes (see, e.g., Bots et al., *J. Cell Sci.,* 119(Pt 24): 5011-4, 2006). The human genes GZMA, GZMB, GZMH, GZMK and GZMM encode granzyme A (e.g., Genbank Accession No. NP_006135.1), granzyme B (e.g., Genbank Accession No. NP_004122.2), granzyme H (e.g., Genbank Accession No. NP_219491.1), granzyme K (e.g., Genbank Accession No. NP_002095.1) and granzyme M (e.g., Genbank Accession No. NP_005308.1), respectively.

Ferritin is a globular protein involved in iron storage. In animals, ferritin is a complex of ferritin light chain (FTL) and ferritin heavy chain (FTH) subunits. Although there are generally 24 subunits in a given ferritin complex, the ratio of FTL to FTH varies from cell type to cell type. FTH has been implicated in regulation of hematopoiesis, hepatocyte apoptosis, cell differentiation and immune function (see, e.g., Recalcati et al., *J Autoimmun.* 2008 30(1-2):84-9, 2008). An exemplary sequence for human FTH is provided in GenBank Accession No. NP_002023.2. An exemplary sequence for human FTL is provided in GenBank Accession No. NP_000137.2. Levels of circulating ferritin are often increased in a multitude of malignancies including cancer (see, e.g., Hazard et al., *Nature.* 265(5596):755-6, 1977).

As used herein, an immune suppressive cytokine is an anti-inflammatory cytokine. Anti-inflammatory cytokines include TGFβ, IL-4, IL-10, IL-13, IL-33, IL-35 and IL-37.

There are at least 30 members in the TGF family, including TGFβ1, TGFβ2 and TGFβ3. TGFβ has been implicated in inhibition of macrophage and Th1 cell activity by suppressing cytokine production. Exemplary TGFs include human TGFβ1 (e.g., Genbank Accession No. NP_000651.3), human TGFβ2 (e.g., Genbank Accession No. NP_001129071.1) and human TGFβ3 (e.g., Genbank Accession No. NP_003230.1).

IL-4 is a cytokine that has been implicated in inhibiting the production of tumour necrosis factor (TNF)-α and IL-1β by lipopolysaccharide (LPS)-activated human monocytes. Exemplary human IL4 sequences are provided at GenBank Accession Numbers NP_000580.1, NP_758858.1 and NP_001341919.1.

IL-10 is a pleiotropic cytokine implicated in immunoregulation and inflammation. IL-10 is mainly produced by monocytes, but can also be produced by lymphocytes and is capable of regulating B cell survival, antibody production and proliferation. IL-10 can act on a receptor complex composed of two IL-10 receptor-1 and two IL-10 receptor-2 proteins. An exemplary human IL-10 sequence is provided at GenBank Accession No. NP_000563.1.

IL-13 is an immunoregulatory cytokine that has been implicated in suppressing inflammatory cytokine production in LPS-activated human monocytes. Exemplary human IL-13 sequences are provided at GenBank Accession Numbers NP_002179.2 and NP_001341920.1. IL-33 belongs to the interleukin 1 superfamily of cytokines, which also includes IL-1α, IL-1β, IL-1RA and IL-18. IL-33 binds to the IL1RL1/ST2 receptor. IL-33 has previously been shown to have an anti-inflammatory role in adipose tissue inflammation and has been shown to have protective effects in cardiovascular diseases. Exemplary human IL-33 sequences are provided under GenBank Accession numbers NP_001300974.1, NP_001186569.1, NP_001186570.1, NP_001300975.1, NP_001300977.1 and NP_001340731.1.

IL-35 is an IL-12 family cytokine. IL-35 is predominantly by produced by regulatory T-cells and is implicated in suppression of the immune system. IL-35 is a heterodimeric protein made of IL-27β and IL12α subunits. Human IL-27β (e.g., GenBank Accession No. NP_005746.2) is encoded by the EBI3 gene. As described above, the human IL12α subunit is encoded by the IL12A gene.

IL-37 is a member of the IL-37 family of cytokines and is implicated in reduction of inflammation. IL-37 is able to inhibit production of many pro-inflammatory cytokines including IL-8, IL-6 and TNFα. Exemplary human IL-37 sequences are provided under GenBank Accession Numbers NP_055254.2, NP_775294.1, NP_775295.1, NP_775296.1 and NP_775297.1.

(ii) Knock-Out Modifications

In some embodiments, the modified immune cells described herein may comprise one or more "knock-out" modifications targeting one or more endogenous inflammatory proteins as described herein. A knock-out modification refers to any type of genetic modifications to a host cell (e.g., immune cells as described herein) that results in reduced production of a target endogenous protein (e.g., a cytokine or other target proteins as described herein) as compared to a wild-type host cell of the same type absent such genetic modification (i.e., wild-type counterpart). Reduced or elevated production of a protein of interest as described herein can be determined by comparing the production levels of the protein of interest by a population of cells of interest with that of a population of control cells (e.g., a population of modified immune cells as described herein versus a population of the wild-type counterpart), which are measured using the same number of cells under the same conditions (e.g., by the same assay using the same experimental conditions). In some instances, the immune cells thus modified may produce lower levels of the target cytokine when activated (e.g., stimulated with an antigen, a receptor agonist or with a cytokine), as compared to the wild-type counterpart activated under the same conditions. Alternatively, the level of cytokine production may be measured without activating the immune cells. In some instances, the level of a particular cytokine produced by the modified cells may not be detectable via a conventional assay. Cytokine levels may be measured using a conventional method known in the art. For example, an ELISA-type assay with a cytokine-specific antibody may be suitable for measurement of cytokine levels.

A knock-out modification may include genetic editing of at least one endogenous allele of a target inflammatory protein, including, but not limited to, an insertion, deletion, or replacement within a coding region of the endogenous allele or a non-coding regulatory region of the endogenous allele, to disrupt expression of the target cytokine. As used herein, an endogenous allele is a gene allele that is naturally found within a cell (i.e., native to a cell).

Alternatively, a knock-out modification may include introducing an exogenous nucleic acid (e.g., an antisense oligonucleotide such as an interfering RNA) that suppresses expression of a target inflammatory protein as described herein. An exogenous nucleic acid refers to a nucleic acid that is not produced by the host cell before modification and is delivered into the host cell via a transfection approach, e.g., those described herein.

Target inflammatory proteins subject to the knock-out modification as described herein include, but are not limited to, inflammatory cytokines or soluble receptors thereof (e.g., IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, and VWF), inflammatory growth factors (e.g., TGFα, VEGF, EGF, HGF, and FGF) and cytotoxic molecules (e.g., perforin, granzyme, and ferritin).

The modified immune cells having the knock-out modifications as described herein may have one or more of the target cytokines/proteins noted above knocked-out. In some instances, an endogenous gene encoding the target cytokine/protein is subject to gene editing in either a coding region or a non-coding regulatory region such that expression of the target cytokine/protein from that endogenous gene disrupted so as to reduce the production level of such a target cytokine/protein by the modified immune cells. In other instances, an exogenous antisense nucleic acid specific to a coding region of the target cytokine/protein (e.g., targeting a suitable region of the mRNA coding for the target cytokine/protein) can be used to modify the immune cells so as to reduce expression of the target cytokine/protein.

The modified immune cells may contain one type of genetic modification as described herein or a combination of different genetic modifications (e.g., a combination of disruption of an endogenous gene for one target cytokine/protein and delivery of an exogenous antisense nucleic acid to down-regulate expression of another target cytokine/protein).

(iii) Knock-In Modifications

In other embodiments, the modified immune cells described herein may comprise one or more "knock-in" modifications to express immune suppressive cytokines or to express antagonists targeting one or more inflammatory proteins (target proteins), for example, inflammatory proteins produced by the immune system of a recipient of adoptive immune cell therapy. Target proteins include inflammatory cytokines, soluble receptors thereof, inflammatory growth factors and cytotoxic molecules. Knock-in modifications may comprise delivering to host cells (e.g., immune cells as described herein) exogenous nucleic acids coding for the immune suppressive cytokines and/or cytokine antagonists. The exogenous nucleic acids are in operative linkage to suitable promoters such that the encoded proteins (e.g., cytokine antagonists and/or immune suppressive cytokines) can be expressed in the host cells. In some instances, the exogenous nucleic acids coding for the antagonists and/or immune suppressive cytokines may integrate into the genome of the host cells. In other instances, the exogenous nucleic acids may remain extrachromosomal (not integrated into the genome).

Examples of target inflammatory proteins include, but are not limited to, are not limited to, inflammatory cytokines or soluble receptors thereof (e.g., IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, and VWF), inflammatory growth factors (e.g., TGFα, VEGF, EGF, HGF, and FGF) and cytotoxic molecules (e.g., perforin, granzyme, and ferritin).

The modified immune cells comprising one or more knock-in modifications may comprise one or more exogenous nucleic acids (e.g., exogenous expression cassettes) for expressing immune suppressive cytokines and/or antagonists of one or more target inflammatory proteins as described herein. For purpose of the present disclosure, it will be explicitly understood that the term "antagonist" encompass all the previously identified terms, titles, and functional states and characteristics whereby the target protein itself, a biological activity of the target protein, or the consequences of the biological activity, are substantially nullified, decreased, or neutralized in any meaningful degree, e.g., by at least 20%, 50%, 70%, 85%, 90%, or above.

In some embodiments, the cytokine antagonists described herein may be an antibody specific to the target protein, an antibody specific to a receptor of the target protein or an antibody to an accessory protein involved in the complex of a cytokine and its receptor. Such antibodies (antagonistic antibodies) also interfere with binding of the target cytokine to its cognate receptor on immune cells, thereby suppressing cell signaling mediated by the target protein. Antagonistic antibodies within the scope of the present disclosure include, but are not limited to, antibodies capable of binding to and neutralize the activity of inflammatory proteins (e.g., inflammatory cytokines including IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, and VWF, inflammatory growth factors including TGFα, VEGF, EGF, HGF, and FGF and cytotoxic molecules, including perforin, granzyme, and ferritin) and antibodies capable of binding to a receptor of any of the target proteins where applicable. Exemplary antagonistic antibodies include clazakizumab, olokizumab, siltuximab, sirukumab (anti-IL6), tocilizumab (anti-IL6R) and sarilumab (anti-IL6R), or antigen-binding fragments thereof, genetically modified versions thereof (e.g., scFv derived from the reference antibody). A genetically modified version of a known antibody (e.g., a scFv antibody) comprises the same heavy chain and light chain complementary determining regions, and optionally comprises the same heavy chain and light variable regions, as the reference antibody.

An antibody (interchangeably used in plural form) as used herein is an immunoglobulin molecule capable of specific binding to a target protein, e.g., IL6 and others described herein, through at least one antigen recognition site, located in the variable region of the immunoglobulin molecule. As used herein, the term "antibody" encompasses not only intact (i.e., full-length) antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

In some embodiments, the antibodies described herein may specifically bind a target protein or a receptor thereof. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target cytokine if it binds with greater affinity, avidity, more readily, and/or with greater duration than it binds to other substances. For example, an antibody that specifically (or preferentially) binds to an IL6 epitope is an antibody that binds this IL6 epitope with greater affinity, avidity, more readily, and/or with greater duration than it binds to other IL6 epitopes or non-IL6 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In some embodiments, an antagonistic antibody of a target protein as described herein has a suitable binding affinity for the target protein (e.g., IL6 or GM-CSF) or antigenic epitopes thereof. As used herein, "binding affinity" refers to the apparent association constant or KA. The KA is the reciprocal of the dissociation constant (KD). The antagonistic antibody described herein may have a binding affinity (KD) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased KD. Higher affinity binding of an antibody for a first antigen relative to a second antigen can be indicated by a higher KA (or a smaller numerical value KD) for binding the first antigen than the KA (or numerical value KD) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the antagonistic antibodies described herein have a higher binding affinity (a higher KA or smaller KD) to the target protein in mature form as compared to the binding affinity to the target protein in precursor form or another protein, e.g., an inflammatory protein in the same family as the target protein. Differences in binding affinity (e.g., for specificity or other comparisons) can be at least 1.5, 2, 3, 4, 5, 10, 15, 20, 37.5, 50, 70, 80, 91, 100, 500, 1000, 10,000 or 105 fold.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

[Bound]=[Free]/(Kd+[Free])

It is not always necessary to make an exact determination of KA, though, since sometimes it is sufficient to obtain a quantitative measurement of affinity, e.g., determined using a method such as ELISA or FACS analysis, is proportional to KA, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some examples, the antagonistic antibodies described herein are human antibodies or humanized antibodies. Alternatively or in addition, the antagonistic antibodies are single-chain antibodies (scFv).

In other embodiments, inflammatory protein antagonists described herein may be soluble receptors capable of binding a target protein. Such soluble receptors may comprise the extracellular domain of a receptor of the target protein but lack transmembrane domains of the receptor such that the soluble receptors do not display on cell surface. A soluble receptor may compete against cell surface receptors from binding to the target protein, thereby suppressing the signaling mediated by the target protein. Exemplary soluble receptors for use in the present disclosure include soluble IL-6 receptor (IL6R), soluble IL1 receptor type II (sIL-1RII), soluble gp130, soluble RAGE, soluble IL15Ra (sIL-15Ra, see e.g., Mortier et al., *J Immunol.* 173(3):1681-8, 2004), and a soluble CCR2 receptor (see, e.g., e.g., Izhak et al., *J Immunol.*, 183(1):732-9, 2009). The interuleukin-1 receptor type 2 (a.k.a. IL-1RII) is encoded by the IL1R2 gene in humans and is implicated as a decoy receptor and acts as an inhibitor of its ligands. Exemplary human IL-1RII sequences are provided under GenBank Accession Numbers NP_004624.1 and NP_001248348.1. As used herein, sIL-1RII refers to the soluble form of the IL-1RII receptor. The modified immune cells comprising knock-in modifications comprise one or more exogenous nucleic acids coding for one or more inflammatory protein antagonists as described herein. In some instances, the exogenous nucleic acid comprises an expression cassette in which the coding sequence is in operable linkage to a suitable promoter (functional in the immune cells to drive expression of the antagonist). Optionally, the expression cassette may comprise one or more regulatory elements, for example, enhancers, polyA regulatory sequences, etc. In some examples, the expression cassette may be part of a viral vector (e.g., a retroviral vector or an AAV vector), for delivery of the exogenous nucleic acids into immune cells and/or for integration into the host genome.

(iv) Cell Populations Comprising Modified Immune Cells

Also provided herein is a population of immune cells comprising modified cells having knock-in modifications, knock-out modifications, or a combination thereof as described herein. The immune cells can be T-cells, NK cells, dendritic cells, macrophages, B cells, neutrophils, eosinophils, basophils, mast cells, myeloid-derived suppressor cells, mesenchymal stem cells, precursors thereof, or combinations thereof. In some instances, the population of immune cells is modified to express a chimeric antigen receptor (CAR), which may specific to an antigen of disease cells, for example, a tumor antigen. A typical CAR construct may comprise an extracellular antigen binding fragment (e.g., a scFv fragment) capable of binding an antigen of interest (for example, a tumor antigen), a transmembrane domain, a co-stimulatory signaling domain, and CD3ζ. Such a CAR construct may further contain a hinge domain.

Alternatively or in addition, the immune cells may be further modified to express an exogenous cytokine, a chimeric antigen receptor (e.g., a chimeric synNotch receptor, a chimeric immunoreceptor, a chimeric costimulatory receptor, a chimeric killer-cell immunoglobulin-like receptor (KIR)), exogenous T cell receptor (TCR) and/or having the endogenous TCR knocked out. A chimeric antigen receptor (CAR) typically comprises (i) an extracellular ligand-binding domain (e.g., a scFv fragment or an extracellular domain of a receptor such as a cytokine receptor, a co-stimulatory receptor, e.g., CD28, or a checkpoint receptor, e.g., PD-1), which is capable of binding to a target protein, (ii) a transmembrane domain for anchoring the CAR on cell membrane, and (iii) one or more intracellular signaling domains for signaling transduction, e.g., the signaling domain of CD3z, KIR, 2B4, CD28, 4-1BB, CD27, OX40, ICOS, MYD88, IL2 receptor, SynNotch, etc. A chimeric cytokine receptor refers to a CAR comprising an extracellular domain of a cytokine receptor. A chimeric costimulatory receptor refers to a CAR comprising an extracellular domain of a costimulatory receptor. A chimeric KIR receptor and chimeric SynNotch receptor refer to CARs comprising a signaling domain from KIR and SynNotch, respectively.

In some embodiments, the population of immune cells described herein may comprise at least (i) a first plurality of modified immune cells, which comprise one or more of the knock-out modifications described herein, and (ii) a second plurality of modified immune cells, which comprise one or more of the knock-out modifications as also described herein.

The first plurality of modified immune cells may produce a reduced level of one or more of the cytokines/proteins as described herein in connection with knock-out modifications, e.g., IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, VWF, TGFα, VEGF, EGF, HGF, and FGF, perforin, granzyme, and ferritin. Some or all members of the first plurality of modified immune cells may harbor one knock-out modification to reduce production of inflammatory protein of interest. Alternatively, some or all members of the first plurality may harbor more than one knock-out modifications to reduce the production of more than one cytokines of interest. Different members of the first plurality of modified immune cells may harbor different or different combination of knock-out modifications. For example, one member may harbor knock-out of IL-2, another member may harbor knock-out of GM-CSF, and a third member may harbor both. All members of the first plurality of modified immune cells, collectively, harbor all of the knock-out modifications of interest such that the production levels of all cytokines of interest are reduced.

The second plurality of modified immune cells may express one or more of antagonists of the one or more target proteins as described herein in connection with the knock-in modifications, for example, an antagonist of IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, VWF, TGFα, VEGF, EGF, HGF, FGF, perforin, granzyme, ferritin or a combination thereof. Some or all members of the second plurality of modified immune cells may harbor one knock-in modification, i.e., carry one exogenous nucleic acid, which may be designed to express one cytokine antagonist of interest, one immune suppressive cytokine of interest, multiple antagonists of interest, multiple immune suppressive cytokines of interest or a combination thereof. Alternatively, some or all members of the second plurality may harbor more than one knock-in modifications, i.e., carry more than one exogenous nucleic acids, each may be designed for expressing one cytokine antagonist, one immune suppressive cytokine, more than one cytokine antagonist, more than one immune suppressive cytokine or a combination thereof. Different members of the second plurality of modified immune cells may harbor different or different combination of knock-in modifications. For example, one member may harbor knock-in of an IL6 antagonist, another member may harbor knock-in of an IL15 antagonist, and a third member may harbor both. All members of the second plurality of modified immune cells, collectively, harbor all of the knock-in modifications of interest such that all antagonists of interest are expressed.

In the population of immune cells comprising the first and second pluralities of modified immune cells, the total level of one or more of such cytokines/proteins produced thereby is reduced by at least 10% (e.g., at least 20%, at least 30%, at least 40%, at least 50%, at least 50%, at least 60%, at least 70%, at least 80% or at least 90%) relative to the total level of the same cytokine(s)/protein(s) produced by a wild-type counterpart (of the same cell number) as determined under the same conditions (e.g., using the same assay and the same experimental conditions). The total level of the cytokine/protein production may represent the production level of such by the immune cells upon activation. Alternatively, the total level of the cytokine/protein production may represent the production level of such by the inactivated immune cells. In some instances, the level of a particular cytokine produced by the population of immune cells may not be detectable by a conventional assay.

Further, the population of immune cells may produce one or more cytokine antagonists at a suitable level for suppressing the signaling mediated by the target cytokine by a meaningful level so as to reduce or eliminate side effects caused by such cytokines in adoptive immune cell therapy.

The first plurality and second plurality of modified immune cells in the immune cell population as described herein may be of the same immune cell type (e.g., T cells or NK cells). In some instances, the first plurality and second plurality of modified immune cells may overlap, i.e., having members possessing both the knock-in and knock-out modifications. In other instances, the first plurality and second plurality of modified immune cells have no overlapping members.

In another embodiments, provided herein is a population of immune cells comprising a plurality of modified immune cells having a knock-out modification of IL-2. In some instances, the total level of IL-2 produced by such an immune cell population can be reduced by at least 10% (e.g., at least 20%, at least 30%, at least 40%, at least 50%, at least 60%, at least 70%, at least 80%, at least 90%, at least 95% or greater) relative to a wild-type counterpart as determined under the same conditions. For example, the total level of IL-2 produced by the immune cell population as described herein may be about 30-95% less than the wild-type counterpart as determined under the same conditions. In one particular example, the total level of IL-2 produced by the immune cell population may be about 50% that of a wild-type counterpart.

The immune cell population may further comprise modified cells harboring additional knock-out and/or knock-in modifications as described herein such that the total level of the knock-out cytokines/proteins is reduced relative to a wild-type counterpart and/or a suitable level of cytokine antagonists is expressed by the immune cell population. In some instances, the immune cell population further comprises modified cells having GM-CSF knocked-out, having TNFα knocked-out, and/or having antagonists of IL6 knocked-in. Similarly, members of the immune cell population may harbor one or more of the knock-in and/or knock-out modifications and different members may harbor different or different combination of the knock-in/knock-out modifications. All members of the immune cell population, collectively, harbor all of the knock-in/knock-out modifications of interest.

II. Method of Preparing Modified Immune Cells

Any of the knock-in and knock-out modifications may be introduced into suitable immune cells by routine methods and/or approaches described herein. Typically, such methods would involve delivery of genetic material into the suitable immune cells to either down-regulate expression of a target endogenous inflammatory protein, express a cytokine antagonist of interest or express an immune suppressive cytokine of interest.

(i) Knocking Out Modification

Any methods known in the art for down-regulating the expression of an endogenous gene in a host cell can be used to reduce the production level of a target endogenous cytokine/protein as described herein.

In some instances, a gene editing method can be performed to modify an endogenous allele of a gene of the target cytokine/protein (e.g., in a coding region or a non-coding regulatory region) so as to reduce expression of the target endogenous cytokines. A gene editing method may involve use of an endonuclease that is capable of cleaving the target region in the endogenous allele. Non-homologous end joining in the absence of a template nucleic acid may repair double-strand breaks in the genome and introduce mutations (e.g., insertions, deletions and/or frameshifts) into a target site. Gene editing methods are generally classified based on the type of endonuclease that is involved in generating double stranded breaks in the target nucleic acid. Examples include, but are not limited to, Clustered Regularly Interspaced Short Palindromic Repeats (CRISPR)/endonuclease systems, transcription activator-like effector-based nuclease (TALEN), zinc finger nucleases (ZFN), endonucleases (e.g., ARC homing endonucleases), meganucleases (e.g., mega-TALs), or a combination thereof.

Cleavage of a gene region may comprise cleaving one or two strands at the location of the target allele by an endonuclease. In some embodiments, the cleavage event may be followed by repairing the cleaved target polynucleotide by homologous recombination with an exogenous template polynucleotide, leading to insertion, deletion, or substitution of one or more nucleotides of the target nucleotide sequence. Such gene editing can result in decreased transcription of a target gene (e.g., IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, VWF, TGFα, VEGF, EGF, HGF, FGF, perforin, granzyme, ferritin or a combination thereof).

The reduction level of a target endogenous cytokine/protein in an immune cell population can be modulated by the level of gene editing event introduced into the cell population. For example, a large amount of one or more gene editing components introduced into a population of host immune cells would result in a large portion of the host immune cells having the target endogenous allele edited. As such, the total production level of the target endogenous cytokine/protein would be reduced by a high level. Alternatively, a small amount of one or more gene editing components introduced into a population of host immune cells would result in a small portion of the host immune cells having the target endogenous allele edited. As such, the total production level of the target endogenous cytokine/protein would be reduced by a low level. Thus, controlling the amount of one or more gene editing components to be delivered to a cell population could control the total reduction level of the target endogenous cytokine/protein. Other suitable approaches may also be applicable to control the reduction level of a target cytokine/protein, as known to those skilled in the art.

In some instances, genetic modification of immune cells as described herein is performed using the Clustered Regularly Interspaced Short Palindromic Repeats (CRISPR)/endonuclease technology known in the art. The CRISPR/endonuclease systems have been adapted for use in both prokaryotic and eukaryotic cells. Gene editing with CRISPR generally relies on expression of at least two components: a guide RNA sequence that recognizes a target nucleic acid sequence and an endonuclease (e.g., including Cpf1 and Cas9). A guide RNA helps direct an endonuclease to a target site, which typically contains a nucleotide sequence that is complementary (partially or completely) to the gRNA or a portion thereof. In some instance, the guide RNA is a two-piece RNA complex comprises a protospacer fragment that is complementary to the target nuclei acid sequence and a scaffold RNA fragment. In some instances, the scaffold RNA is required to aid in recruiting the endonuclease to the target site. In some instances, the guide RNA is a single guide RNA (sgRNA) that comprises both the protospacer sequence and the scaffold RNA sequence. An exemplary sequence of the scaffold RNA can be: GUUUUAGAGC-UAGAAAUAGCAAGUUAAAAUAAGGCUAGU-CCGUUAUCAACUUGA AAAAGUGGCACCGAGUCG-GUGCUUUU (SEQ ID NO: 31). Once at the target site, the endonuclease can generate a double strand break. It would have been known to those skilled in the art that nucleotide sequences for RNA molecules include residue "U." The corresponding DNA sequence of any of the RNA sequences disclosed herein is also within the scope of the present disclosure. Such a DNA sequence would include "T" in replacement of "U" in the corresponding RNA sequence.

The target nucleic acid for use with the CRISPR system is flanked on the 3' side by a protospacer adjacent motif (PAM) that may interact with the endonuclease and be further involved in targeting the endonuclease activity to the target nucleic acid. It is generally thought that the PAM sequence flanking the target nucleic acid depends on the endonuclease and the source from which the endonuclease is derived. For example, for Cas9 endonucleases that are derived from *Streptococcus pyogenes*, the PAM sequence is NGG. For Cas9 endonucleases derived from *Staphylococcus aureus*, the PAM sequence is NNGRRT. For Cas9 endonucleases that are derived from *Neisseria meningitidis*, the PAM sequence is NNNNGATT. For Cas9 endonucleases derived from *Streptococcus thermophilus*, the PAM sequence is NNAGAA. For Cas9 endonuclease derived from *Treponema denticola*, the PAM sequence is NAAAAC. For a Cpf1 nuclease, the PAM sequence is TTN.

A CRISPR/endonuclease system that hybridizes with a target sequence in the locus of an endogenous cytokine may be used to knock out the cytokine of interest. A gRNA hybridizes to (complementary to, partially or completely) a target nucleic acid sequence (e.g., the endogenous locus of a cytokine) in the genome of a host cell. The gRNA or portion thereof that hybridizes to the target nucleic acid may be between 15-25 nucleotides, 18-22 nucleotides, or 19-21 nucleotides in length. In some instances, the gRNA sequence that hybridizes to the target nucleic acid is 15, 16, 17, 18, 19, 20, 21, 22, 23, 24, or 25 nucleotides in length. In some examples, the gRNA sequence that hybridizes to the target nucleic acid is between 10-30, or between 15-25, nucleotides in length.

In some examples, the gRNA sequence is at least 50%, 55%, 60%, 65%, 70%, 75%, 80%, 85%, 90%, 95%, 96%, 97%, 98%, 99%, or at least 100% complementary to a target nucleic acid (see also U.S. Pat. No. 8,697,359, which is incorporated by reference for its teaching of complementarity of a gRNA sequence with a target polynucleotide sequence). It has been demonstrated that mismatches between a CRISPR guide sequence and the target nucleic acid near the 3' end of the target nucleic acid may abolish nuclease cleavage activity (see, e.g., Upadhyay, et al. Genes Genome Genetics (2013) 3(12):2233-2238). In some examples, the gRNA sequence is at least 50%, 55%, 60%, 65%, 70%, 75%, 80%, 85%, 90%, 95%, 96%, 97%, 98%, 99%, or at least 100% complementary to the 3' end of the target nucleic acid (e.g., the last 5, 6, 7, 8, 9, or 10 nucleotides of the 3' end of the target nucleic acid).

The "percent identity" of two nucleic acids is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST nucleotide searches can be performed with the NBLAST program, score=100, wordlength-12 to obtain nucleotide sequences homologous to the nucleic acid molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some instances, the amount of one or more guide RNAs or sgRNAs introduced into a population of cells reduces overall production of one or more inflammatory proteins (e.g IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, VWF, TGFα, VEGF, EGF, HGF, FGF, perforin, granzyme, ferritin or a combination thereof) by the population by at least 10% (at least 20%, at least 30%, at least 40%, at least 50%, at least 60%, at least 70%, at least 80% or least 90%) compared to a wildtype population without the one or more guide RNAs or sgRNAs. For example, the amount of a sgRNA in a CRISPR/CAS system targeting the IL-2 locus may result in the overall population producing about 30-95% less IL-2. In one example, the IL-2 production is reduced by about 50%. The CRISPR/endonuclease system may optionally be used to modify the endogenous GM-CSF locus and/or TNF locus to reduce production of these cytokines.

A variety of CRISPR/endonuclease systems are known in the art and modifications are regularly and numerous references describe rules and parameters that are used to guide the design of CRISPR/endonuclease systems (e.g., including Cas9 target selection tools). See, e.g., Hsu et al., Cell, 157(6):1262-78, 2014.

In some instances, genetic modification of the immune cells as described herein is performed using the TALEN technology known in the art. TALENs are engineered restriction enzymes that can specifically bind and cleave a desired target DNA molecule. A TALEN typically contains a Transcriptional Activator-Like Effector (TALE) DNA-binding domain fused to a DNA cleavage domain. The DNA binding domain may contain a highly conserved 33-34 amino acid sequence with a divergent 2 amino acid RVD (repeat variable dipeptide motif) at positions 12 and 13. The RVD motif determines binding specificity to a nucleic acid sequence and can be engineered according to methods known to those of skill in the art to specifically bind a desired DNA sequence (see, e.g., Juillerat et al., Scientific reports, 5:8150, 2015; Miller et. al., Nature Biotechnology 29 (2): 143-8, 2011; Zhang et. al. Nature Biotechnology 29 (2): 149-53, 2011; Geipler et al., PLoS ONE 6 (5): e19509, 2011; Boch, Nature Biotechnology 29 (2): 135-6, 2011; Boch, et. al., Science 326 (5959): 1509-12, 2009; and Moscou et al., Science 326 (5959): 1501, 2009. The DNA cleavage domain may be derived from the FokI endonuclease, which is active in many different cell types. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. See, e.g., Miller et al., *Nature Biotech.* 29: 143-8, 2011.

TALENs specific to sequences in a target gene of interest (e.g., IL2, IL1α, IL1β, IL-5, IL-6, IL-7, IL-8, IL-9, IL-12, IL-15, IL-17, IL-18, IL-21, IL-23, sIL-1RI, sIL-2Rα, sIL6R, IFNα, IFNβ, IFNγ, MIPα, MIPβ, CSF1, LIF, G-CSF, GM-CSF, CXCL10, CCL5, eotaxin, TNF, MCP1, MIG, RAGE, CRP, angiopoietin-2, VWF, TGFα, VEGF, EGF, HGF, FGF, perforin, granzyme, ferritin or a combination thereof) can be constructed using any method known in the art, including various schemes using modular components. See, e.g., Zhang et al. Nature Biotech. 29, 2011: 149-53; and Geibler et al., PLoS ONE 6: e19509, 2011.

A TALEN specific to a target gene of interest can be used inside a cell to produce a double-stranded break (DSB). A mutation can be introduced at the break site if the repair mechanisms improperly repair the break via non-homologous end joining. For example, improper repair may introduce a frame shift mutation.

In some examples, zinc finger nucleases (ZFNs), which are known in the art, may be used to generate a population of modified immune cells described herein. Zinc finger nucleases (ZFNs) are restriction enzymes comprised of an engineered zinc finger DNA binding domain linked to the catalytic domain of the type II endonuclease FokI. The zinc finger DNA binding domain of each ZFN targets the linked FokI endonuclease to a specific site in the genome. Since FokI functions only as a dimer, a pair of ZFNs is typically engineered to bind to cognate target "half-site" sequences on opposite DNA strands. The target "half-site" sequences are generally spaced such the catalytically active FokI dimer may form between them. Upon dimerization of the FokI domain, a DNA double-strand break is generated between the ZFN half-sites. As mentioned above, non-homologous end joining may introduce mutations, while homology-directed repair may be used to introduce an exogenous nucleic acid.

Many gene editing systems using ZFNs and considerations for design of ZFNs have been described; see, e.g., Segal et al., Proc Natl Acad Sci USA 96(6):2758-63, 1999; Dreier B et al., J Mol Biol. 303(4):489-502, 2000; Liu Q et al., J Biol Chem. 277(6):3850-6, 2002; Dreier et al., J Biol Chem 280(42):35588-97, 2005; and Dreier et al., J Biol Chem. 276(31):29466-78, 2001.

Meganucleases (or homing endonucleases), which are sequence-specific endonucleases that recognize long DNA targets (often between 14 and 40 base pairs) may also be introduced using any method known in the art to genetically engineer any of the modified cells described herein. There are at least six families of meganucleases and they are often classified based on structural motifs, including LAGLI-DADG, GIY-YIG, HNH, His-Cys box, PD-(D/E)XK and Vsr-like. Non limiting examples of meganucleases include PI-SceI, I-CreI and I-TevI.

Various gene editing systems using meganucleases, including modified meganucleases, have been described in the art; see, e.g., the reviews by Steentoft et al., Glycobiology 24(8):663-80, 2014; Belfort and Bonocora, Methods Mol Biol. 1123:1-26, 2014; Hafez and Hausner, Genome 55(8):553-69, 2012; and references cited therein.

Hybrid nucleases including MegaTAL may also be used. MegaTALs are a fusion of a TALE DNA binding domain with a catalytically active meganuclease. Such nucleases harness the DNA binding specificity of TALEs and the sequence cleavage specificity of meganucleases. See, e.g., Boissel et al., NAR, 42: 2591-2601, 2014.

Alternatively, any of the knock-out modification may be achieved using antisense oligonucleotides or ribozymes via methods known in the art. An antisense oligonucleotide specific to a target cytokine/protein refers to an oligonucleotide that is complementary or partially complementary to a target region of an endogenous gene of the cytokine or an mRNA encoding such.

Antisense oligonucleotides may include small interfering RNA (siRNA or RNAi), which may down-regulate expression of a target cytokine via RNA interference. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains)

or a short hairpin RNA (i.e., a RNA chain forming a tight hairpin structure), both of which can be designed based on the sequence of the target gene. Alternatively, it can be a microRNA.

Any of the antisense oligonucleotides or an expression cassette for producing such may be delivered into immune cells via conventional methods to down-regulate the production of one or more target cytokines/proteins as described herein.

(ii) Knocking-In Modification

To generate a knock-in of one or more cytokine antagonists described herein, a coding sequence of any of the antagonists and/or immune suppressive cytokines described herein may be cloned into a suitable expression vector (e.g., including but not limited to lentiviral vectors, retroviral vectors, adenovivral vectors, adeno-associated vectors, PiggyBac transposon vector and SleepingBeauty transposon vector) and introduced into host immune cells using conventional recombinant technology. Sambrook et al., Molecular Cloning, A Laboratory Mannual, 3rd Ed., Cold Spring Harbor Laboratory Press. As a result, modified immune cells of the present disclosure may comprise one or more exogenous nucleic acids encoding at least one cytokine antagonist or at least one immune suppressive cytokine. In some instances, the coding sequence of one or more antagonists and/or one or more immune suppressive cytokines is integrated into the genome of the cell. In some instances, the coding sequence of one or more antagonists is not integrated into the genome of the cell.

An exogenous nucleic acid comprising a coding sequence of a cytokine antagonist or an immune suppressive cytokine of interest may further comprise a suitable promoter, which can be in operable linkage to the coding sequence. A promoter, as used herein, refers to a nucleotide sequence (site) on a nucleic acid to which RNA polymerase can bind to initiate the transcription of the coding DNA (e.g., for a cytokine antagonist) into mRNA, which will then be translated into the corresponding protein (i.e., expression of a gene). A promoter is considered to be "operably linked" to a coding sequence when it is in a correct functional location and orientation relative to the coding sequence to control ("drive") transcriptional initiation and expression of that coding sequence (to produce the corresponding protein molecules). In some instances, the promoter described herein can be constitutive, which initiates transcription independent other regulatory factors. In some instances, the promoter described herein can be inducible, which is dependent on regulatory factors for transcription. Exemplary promoters include, but are not limited to ubiquitin, RSV, CMV, EF1α and PGK1. In one example, one or more nucleic acids encoding one or more antagonists of one or more inflammatory cytokines as those described herein, operably linked to one or more suitable promoters can be introduced into immune cells via conventional methods to drive expression of one or more antagonists.

Additionally, the exogenous nucleic acids described herein may further contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Suitable methods for producing vectors containing transgenes are well known and available in the art. Sambrook et al., Molecular Cloning, A Laboratory Mannual, 3rd Ed., Cold Spring Harbor Laboratory Press.

(iii) Preparation of Immune Cell Population Comprising Modified Immune Cells

A population of immune cells comprising any of the modified immune cells described herein, or a combination thereof, may be prepared by introducing into a population of host immune cells one or more of the knock-out modifications, one or more of the knock-in modifications, or a combination thereof. The knock-in and knock-out modifications can be introduced into the host cells in any order.

In some instances, one or more modifications are introduced into the host cells in a sequential manner without isolation and/or enrichment of modified cells after a preceding modification event and prior to the next modification event. In that case, the resultant immune cell population may be heterogeneous, comprising cells harboring different modifications or different combination of modifications. Such an immune cell population may also comprise unmodified immune cells. The level of each modification event occurring in the immune cell population can be controlled by the amount of genetic materials that induce such modification as relative to the total number of the host immune cells. See also above discussions.

In other instances, modified immune cells may be isolated and enriched after a first modification event before performing a second modification event. This approach would result in the production of a substantially homogenous immune cell population harboring all of the knock-in and/or knock-out modifications introduced into the cells.

In some examples, the knock-in modification(s) and the knock-out modification(s) are introduced into host immune cells separately. For example, a knock-out modification is performed via gene editing to knock out an endogenous gene for a target cytokine and a knock-in modification is performed by delivering into the host immune cells a separate exogenous expression cassette for producing one or more cytokine antagonists. An exemplary schematic is provided in FIG. 1, left panel.

Alternatively, a knock-in modification and a knock-out modification may be performed simultaneously as illustrated in FIG. 1, right panel. For example, an exogenous nucleic acid encoding one or more cytokine antagonists may be introduced through homologous donor template along with the gene editing systems described above to knock in one or more cytokine antagonists of interest and at the same time, knock out an endogenous gene allele to reduce the production of an endogenous cytokine/protein as described herein. When the CRISPR/endonuclease system is used, a guide RNA may be designed to target an endogenous locus of a cytokine of interest, and at the time, to introduce an expression cassette for producing one or more cytokine antagonists of interest.

Alternatively, an exogenous nucleic acid (e.g., an expression cassette encoding a cytokine antagonist) can be introduced into the cell along with the TALEN. This process can be used to introduce a DNA fragment into a target gene of interest and/or introduce a defect into the endogenous gene, thus decreasing expression of the target gene, and at the time, introducing an exogenous nucleic acid for expressing one or more cytokine antagonists.

The immune cell population can be further modified to express an exogenous cytokine, a chimeric antigen receptor (CAR) as described herein, such as a chimeric cytokine receptor, a chimeric synNotch receptor, a chimeric immunoreceptor, a chimeric costimulatory receptor, a chimeric killer-cell immunoglobulin-like receptor (KIR), and/or an exogenous T cell receptor. This can be done either before, after, or concurrently with the knock-in and/or knock-out modifications. Such receptors may be cloned and integrated into any suitable expression vector using routine recombinant technology. Considerations for design of chimeric antigen receptors are also known in the art. See, e.g., Sadelain et al., Cancer Discov., 3(4):388-98, 2013.

III. Therapeutic Applications

Any of the immune cell populations comprising the modified immune cells as described herein may be used in an adoptive immune cell therapy for treating a target disease, such as leukemia or lymphoma. Due to the knock-in and knock-out modifications introduced in to the immune cells, the therapeutic uses of such would be expected to reduce cytotoxicity associated with conventional adoptive immune cell therapy (reducing inflammatory cytokine production and/or signaling by both the immune cells used in adoptive immune cell therapy and endogenous immune cells of the recipient, which can be activated by the infused immune cells), while achieving the same or better therapeutic effects.

To practice the therapeutic methods described herein, an effective amount of the immune cell population, comprising any of the modified immune cells as described herein, may be administered to a subject who needs treatment via a suitable route (e.g., intravenous infusion). The immune cell population may be mixed with a pharmaceutically acceptable carrier to form a pharmaceutical composition prior to administration, which is also within the scope of the present disclosure. The immune cells may be autologous to the subject, i.e., the immune cells are obtained from the subject in need of the treatment, modified to reduce expression of one or more target cytokines/proteins, for example, those described herein, to express one or more cytokine antagonists described herein, to express a CAR construct and/or exogenous TCR, or a combination thereof. The resultant modified immune cells can then be administered to the same subject. Administration of autologous cells to a subject may result in reduced rejection of the immune cells as compared to administration of non-autologous cells. Alternatively, the immune cells can be allogenic cells, i.e., the cells are obtained from a first subject, modified as described herein and administered to a second subject that is different from the first subject but of the same species. For example, allogenic immune cells may be derived from a human donor and administered to a human recipient who is different from the donor.

The subject to be treated may be a mammal (e.g., human, mouse, pig, cow, rat, dog, guinea pig, rabbit, hamster, cat, goat, sheep or monkey). The subject may be suffering from cancer, have an infectious disease or an immune disorder. Exemplary cancers include but are not limited to hematologic malignancies (e.g., B-cell acute lymphoblastic leukemia, chronic lymphocytic leukemia and multiple myeloma). Exemplary infectious diseases include but are not to human immunodeficiency virus (HIV) infection, Epstein-Barr virus (EBV) infection, human papillomavirus (HPV) infection, dengue virus infection, malaria, sepsis and *E. coli* infection. Exemplary immune disorders include but are not limited to, autoimmune diseases, such as rheumatoid arthritis, type I diabetes, systemic lupus erythematosus, inflammatory bowel disease, multiple sclerosis, Guillain-Barre syndrome, chronic inflammatory demyelinating polyneuropathy, psoriasis, Graves' disease, Hashimoto's thyroiditis, myasthenia gravis, and vasculitis.

The term "an effective amount" as used herein refers to the amount of each active agent required to confer therapeutic effect on the subject, either alone or in combination with one or more active agents. Effective amounts vary, as recognized by those skilled in the art, depending on the particular condition being treated, the severity of the condition, individual patient parameters including age, physical condition, size, gender and weight, the duration of treatment, route of administration, excipient usage, co-usage (if any) with other active agents and like factors within the knowledge and expertise of the health practitioner. The quantity to be administered depends on the subject to be treated, including, for example, the capacity of the individual's immune system to produce a cell-mediated immune response. Precise mounts of active ingredient required to be administered depend on the judgment of the practitioner. However, suitable dosage ranges are readily determinable by one skilled in the art.

The term "treating" as used herein refers to the application or administration of a composition including one or more active agents to a subject, who has a target disease, a symptom of the target disease, or a predisposition toward the target disease, with the purpose to cure, heal, alleviate, relieve, alter, remedy, ameliorate, improve, or affect the disease, the symptoms of the disease, or the predisposition toward the disease.

The immune cell populations comprising the modified immune cells as described herein may be utilized in conjunction with other types of therapy for cancer, such as chemotherapy, surgery, radiation, gene therapy, and so forth. Such therapies can be administered simultaneously or sequentially (in any order) with the immunotherapy described herein. When co-administered with an additional therapeutic agent, suitable therapeutically effective dosages for each agent may be lowered due to the additive action or synergy.

Non-limiting examples of other anti-cancer therapeutic agents useful for combination with the modified immune cells described herein include, but are not limited to, immune checkpoint inhibitors (e.g., PDL1, PD1, and CTLA4 inhibitors), anti-angiogenic agents (e.g., TNP-470, platelet factor 4, thrombospondin-1, tissue inhibitors of metalloproteases, prolactin, angiostatin, endostatin, bFGF soluble receptor, transforming growth factor beta, interferon alpha, soluble KDR and FLT-1 receptors, and placental proliferin-related protein); a VEGF antagonist (e.g., anti-VEGF antibodies, VEGF variants, soluble VEGF receptor fragments); chemotherapeutic compounds. Exemplary chemotherapeutic compounds include pyrimidine analogs (e.g., 5-fluorouracil, floxuridine, capecitabine, gemcitabine and cytarabine); purine analogs (e.g., fludarabine); folate antagonists (e.g., mercaptopurine and thioguanine); antiproliferative or antimitotic agents, for example, vinca alkaloids; microtubule disruptors such as taxane (e.g., paclitaxel, docetaxel), vincristin, vinblastin, nocodazole, epothilones and navelbine, and epidipodophyllotoxins; DNA damaging agents (e.g., actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide).

In some embodiments, radiation or radiation and chemotherapy are used in combination with the cell populations comprising modified immune cells described herein. Additional useful agents and therapies can be found in Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

IV. Kits for Therapeutic Uses or Making Modified Immune Cells

The present disclosure also provides kits for use of any of the target diseases described herein involving the immune cell population described herein and kits for use in making the modified immune cells as described herein.

A kit for therapeutic use as described herein may include one or more containers comprising an immune cell population, which may be formulated to form a pharmaceutical composition. The immune cell population comprises any of the modified immune cells described herein or a combination thereof. The population of immune cells, such as T lymphocytes, NK cells, and others described herein may further express a CAR construct and/or an exogenous TCR, as described herein.

In some embodiments, the kit can additionally comprise instructions for use of the immune cell population in any of the methods described herein. The included instructions may comprise a description of administration of the immune cell population or a pharmaceutical composition comprising such to a subject to achieve the intended activity in a subject. The kit may further comprise a description of selecting a subject suitable for treatment based on identifying whether the subject is in need of the treatment. In some embodiments, the instructions comprise a description of administering the immune cell population or the pharmaceutical composition comprising such to a subject who is in need of the treatment.

The instructions relating to the use of the immune cell population or the pharmaceutical composition comprising such as described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port. At least one active agent in the pharmaceutical composition is a population of immune cells (e.g., T lymphocytes or NK cells) that comprise any of the modified immune cells or a combination thereof.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

Also provided here are kits for use in making the modified immune cells as described herein. Such a kit may include one or more containers each containing reagents for use in introducing the knock-in and/or knock-out modifications into immune cells. For example, the kit may contain one or more components of a gene editing system for making one or more knock-out modifications as those described herein. Alternatively or in addition, the kit may comprise one or more exogenous nucleic acids for expressing cytokine antagonists as also described herein and reagents for delivering the exogenous nucleic acids into host immune cells. Such a kit may further include instructions for making the desired modifications to host immune cells.

V. General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; Oligonucleotide Synthesis (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); *Introduction to Cell and Tissue Culture* (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higginseds. (1985; *Transcription and Translation* (B. D. Hames & S. J. Higgins, eds. (1984; *Animal Cell Culture* (R. I. Freshney, ed. (1986; *Immobilized Cells and Enzymes* (lRL Press, (1986» and B. Perbal, *A practical Guide To Molecular Cloning* (1984); F. M. Ausubel et al. (eds.).

The present disclosure is not limited in its application to the details of construction and the arrangements of component set forth in the description herein or illustrated in the drawings. The present disclosure is capable of other embodiments and of being practice or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. As also used in this specification and the appended claims, the singular forms "a," "an," and "the" include plural references unless the context clearly dictates otherwise.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1. Expression of an Anti-IL6R Antibody by T Cells Carrying a Knock-in Gene Expression Cassette Successfully Inhibited IL6 Signaling Third generation self-inactivating (SIN) lentiviral vector encoding a single-chain variable fragment (scFv) antibody derived from tocilizumab, which targets IL6R, was generated by Lipofectamine 2000 transfection. The resulting lentiviral vector was then applied in spin transduction (2500 rpm for 90 minutes at room temperature) of Jurkat E6-1 cells (acute T cell leukemia). The transduced cells were expanded and cultured to collect supernatant containing secreted scFv for evaluation of blocking human IL6 pathway signaling using HEK-Blue IL-6 Cells (Invivogen). HEK-Blue IL-6 reporter cells were used because they are capable of producing Secreted Embryonic Alkaline Phosphatase (SEAP) upon human IL6 stimulation. SEAP production was quantified by measuring optical absorbance of converted substrate Quant Blue (Invivogen) at 650 nm wavelength through a spectrophotometer.

Figure 2:
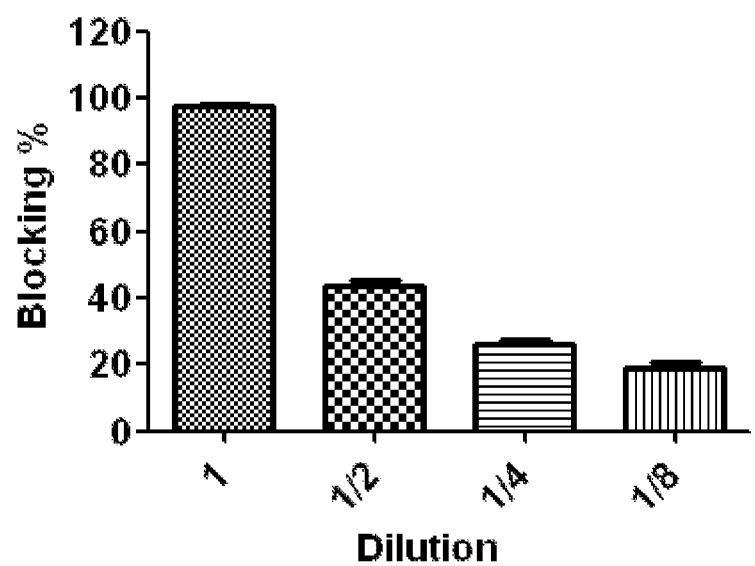
FIG. 2 includes a graph showing the efficiency of Anti-IL6R scFv (derived from tocilizumab) expressed from Jurkat E6-1 cells at blocking IL6-IL6R signaling. An anti-IL6R scFv cassette was knocked in. The negative control used for comparison was the IL6 reporter cells treated with medium. An anti-IL6 antibody was used as a positive control.

As shown in FIG. 2, various dilutions of supernatant from Jurkat T cells, which harbor a knockin gene cassette encoding tocilizumab scFv, were tested. Supernatant from these cells inhibited IL6 activity by binding to the IL6R expressed on the reporter cells. For example, even at ⅛ dilution of supernatant, there was a reduction in IL6 pathway signaling (FIG. 2). These results suggested that the Tocilizumab scFv encoded by the knockin gene cassette was functional and effectively blocked IL6-IL6R signaling.

Example 2. Knock Out of Endogenous Cytokine Genes

Thermo scientific GeneArt Crispr/Cas9 editing kit was used to generate GM-CSF, IL2 and TNF knockouts. Each sgRNA comprises a spacer sequence for targeting a gene site to be edited and a scaffold RNA having the sequence of SEQ ID NO: 31. The spacer sequences were designed by targeting the 19-20 nt sequence (alternatively 17-20 nt) before PAM sequence in the exon I of human GM-CSF, IL2 and TNF gene locus. sgRNAs were synthesized via in vitro transcription by Thermo scientific GeneArt sgRNA synthesis kit. Thermo scientific TrueCut Cas9 Protein v2 was combined with the sgRNA to form Ribonucleoprotein (RNP) complex and introduced to Jurkat cells by a BTX ECM830 electroporator. Successful disruption of gene expression was verified by ELISA kits (BD Biosciences, and R&D systems) around 7 days after electroporation. For ELISA, engineered Jurkat cells were activated overnight by PMA/Inomycin and the supernatant was collected for the analysis of cytokine production. The percent cytokine reduction for each cytokine tested is shown relative to wildtype Jurkat cells with normal secretion of cytokines in FIGS. 3-5.

Figure 3:
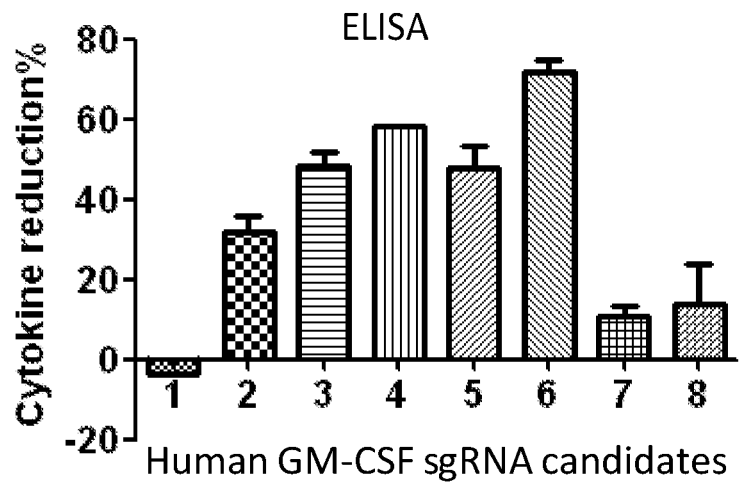
FIG. 3 is a chart showing the gene editing efficiency of various sgRNA candidates targeting the human GM-CSF gene in Jurkat cells, using the CRISPR/CAS9 system, as compared to control cells (with no modification).

Eight sgRNAs targeting human GM-CSF were tested in Jurkat cells. Most of the sgRNAs being tested led to some reduction in the levels of GM-CSF (FIG. 3). For example, sgRNA candidates 3-6 showed more than 40% reduction of GM-CSF levels (FIG. 3). The sequences in human GM-CSF targeted by sgRNA 1-8 are respectively shown by double-strand sequences:

```
                                      (SEQ ID NO: 1)
5'-GCTGCAGAGCCTGCTGCTCT-3'

(SEQ ID NO: 74)
3'-CGACGTCTCGGACGACGAGA-5'

(SEQ ID NO: 2)
5'-GGAGCATGTGAATGCCATCC-3'

(SEQ ID NO: 75)
3'-CCTCGTACACTTACGGTAGG-5'

(SEQ ID NO: 3)
5'-GCATGTGAATGCCATCCAGG-3'

(SEQ ID NO: 76)
3'-CGTACACTTACGGTAGGTCC-5'

(SEQ ID NO: 4)
5'-GAGACGCCGGGCCTCCTGGA-3'

(SEQ ID NO: 77)
3'-CTCTGCGGCCCGGAGGACCT-5'

(SEQ ID NO: 5)
5'-GATGGCATTCACATGCTCCC-3'

(SEQ ID NO: 78)
3'-CTACCGTAAGTGTACGAGGG-5'

(SEQ ID NO: 6)
5'-GCTCCCAGGGCTGCGTGCTG-3'

(SEQ ID NO: 79)
3'-CGAGGGTCCCGACGCACGAC-5'

(SEQ ID NO: 7)
5'-GCGTGCTGGGGCTGGGCGAG-3'

(SEQ ID NO: 80)
3'-CGCACGACCCCGACCCGCTC-5'

(SEQ ID NO: 8)
5'-GCTGGGGCTGGGCGAGCGGG-3'

(SEQ ID NO: 81)
3'-CGACCCCGACCCGCTCGCCC-5'
```

Exemplary protospacer sequences in a gRNA (e.g., a sgRNA) for targeting the above-noted human GM-CSF sites and exemplary sgRNA sequences containing such are provided below (respectively):

```
sgRNA 1 spacer:
                                     (SEQ ID NO: 32)
GCUGCAGAGCCUGCUGCUCU sgRNA 1 whole sequence:
                                     (SEQ ID NO: 33)
GCUGCAGAGCCUGCUGCUCUGUUUUAGAGCUAGAAAUAGCAAGUUAAAAU
AAGGCUAGUCCGUUAUCAACUUGAAAAAGUGGCACCGAGUCGGUGCUUUU sgRNA 2 spacer:
                                     (SEQ ID NO: 34)
GGAGCAUGUGAAUGCCAUCC sgRNA 2 whole sequence:
                                     (SEQ ID NO: 35)
GGAGCAUGUGAAUGCCAUCCGUUUUAGAGCUAGAAAUAGCAAGUUAAAAU
AAGGCUAGUCCGUUAUCAACUUGAAAAAGUGGCACCGAGUCGGUGCUUUU sgRNA 3 spacer:
                                     (SEQ ID NO: 36)
GCAUGUGAAUGCCAUCCAGG
``` sgRNA 3 whole sequence:

(SEQ ID NO: 37)
GCAUGUGAAUGCCAUCCAGGGUUUUAGAGCUAGAAAUAGCAAGUUAAAAU

AAGGCUAGUCCGUUAUCAACUUGAAAAAGUGGCACCGAGUCGGUGCUUUU sgRNA 4 spacer:

(SEQ ID NO: 38)
GAGACGCCGGGCCUCCUGGA sgRNA 4 whole sequence:

(SEQ ID NO: 39)
GAGACGCCGGGCCUCCUGGAGUUUUAGAGCUAGAAAUAGCAAGUUAAAAU

AAGGCUAGUCCGUUAUCAACUUGAAAAAGUGGCACCGAGUCGGUGCUUUU sgRNA 5 spacer:

(SEQ ID NO: 40)
GAUGGCAUUCACAUGCUCCC sgRNA 5 whole sequence:

(SEQ ID NO: 41)
GAUGGCAUUCACAUGCUCCCGUUUUAGAGCUAGAAAUAGCAAGUUAAAAU

AAGGCUAGUCCGUUAUCAACUUGAAAAAGUGGCACCGAGUCGGUGCUUUU sgRNA 6 spacer:

(SEQ ID NO: 42)
GCUCCCAGGGCUGCGUGCUG sgRNA 6 whole sequence:

(SEQ ID NO: 43)
GCUCCCAGGGCUGCGUGCUGGUUUUAGAGCUAGAAAUAGCAAGUUAAAAU

AAGGCUAGUCCGUUAUCAACUUGAAAAAGUGGCACCGAGUCGGUGCUUUU sgRNA 7 spacer:

(SEQ ID NO: 44)
GCGUGCUGGGGCUGGGCGAG sgRNA 7 whole sequence:

(SEQ ID NO: 45)
GCGUGCUGGGGCUGGGCGAGGUUUUAGAGCUAGAAAUAGCAAGUUAAAAU

AAGGCUAGUCCGUUAUCAACUUGAAAAAGUGGCACCGAGUCGGUGCUUUU sgRNA 8 spacer:

(SEQ ID NO: 46)
GCUGGGGCUGGGCGAGCGGG sgRNA 8 whole sequence:

(SEQ ID NO: 47)
GCUGGGGCUGGGCGAGCGGGGUUUUAGAGCUAGAAAUAGCAAGUUAAAAU

AAGGCUAGUCCGUUAUCAACUUGAAAAAGUGGCACCGAGUCGGUGCUUUU

Figure 4:
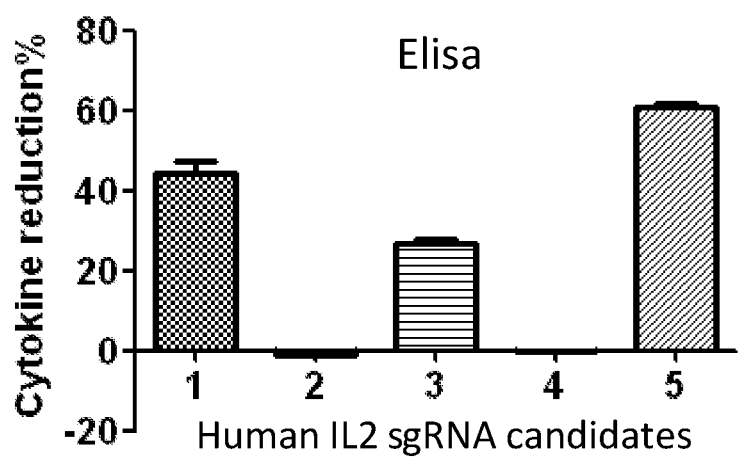
FIG. 4 is a chart showing the gene editing efficiency of various sgRNA candidates targeting the human IL-2 in Jurkat cells, using the CRISPR/CAS9 system, as compared to control cells (with no modification).

Similarly, five sgRNAs targeting human IL2 were also tested in Jurkat cells. As shown in FIG. 4, sgRNA candidates 1, 3 and 5 showed more than 20% reduction of IL2 levels, with sgRNA candidates 1 and 5 showing more than 40% cytokine reduction.

The sequences in human IL2 targeted by sgRNA 1-5 are respectively shown by double-strand sequences:

(SEQ ID NO: 9)
5'-GACTTAGTGCAATGCAAGAC-3'

(SEQ ID NO: 82)
3'-CTGAATCACGTTACGTTCTG-5'

(SEQ ID NO: 10)
5'-GATTTACAGATGATTTTGAA-3'

(SEQ ID NO: 83)
3'-CTAAATGTCTACTAAAACTT-5'

(SEQ ID NO: 11)
5'-AAGAAAACACAGCTACAAC-3'

(SEQ ID NO: 84)
3'-TTCTTTTGTGTCGATGTTG-5'

(SEQ ID NO: 12)
5'-CAACTGGAGCATTTACTGC-3'

(SEQ ID NO: 85)
3'-GTTGACCTCGTAAATGACG-5'

(SEQ ID NO: 13)
5'-TCTTTGTAGAACTTGAAGT-3'

(SEQ ID NO: 86)
3'-AGAAACATCTTGAACTTCA-5'

Exemplary protospacer sequences in a gRNA (e.g., a sgRNA) for targeting the above-noted human IL2 sites and exemplary sgRNA sequences containing such are provided below (respectively):

sgRNA 1 spacer:

(SEQ ID NO: 48)
GACUUAGUGCAAUGCAAGAC sgRNA 1 whole sequence:

(SEQ ID NO: 49)
GACUUAGUGCAAUGCAAGACGUUUUAGAGCUAGAAAUAGCAAGUUAAAAU

AAGGCUAGUCCGUUAUCAACUUGAAAAAGUGGCACCGAGUCGGUGCUUUU sgRNA 2 spacer:

(SEQ ID NO: 50)
GAUUUACAGAUGAUUUUGAA sgRNA 2 whole sequence:

(SEQ ID NO: 51)
GAUUUACAGAUGAUUUUGAAGUUUUAGAGCUAGAAAUAGCAAGUUAAAAU

AAGGCUAGUCCGUUAUCAACUUGAAAAAGUGGCACCGAGUCGGUGCUUUU sgRNA 3 spacer:

(SEQ ID NO: 52)
AAGAAAACACAGCUACAAC sgRNA 3 whole sequence (SEQ ID NO: 53)
AAGAAAACACAGCUACAACGUUUUAGAGCUAGAAAUAGCAAGUUAAAAUA

AGGCUAGUCCGUUAUCAACUUGAAAAAGUGGCACCGAGUCGGUGCUUUU sgRNA 4 spacer:

(SEQ ID NO: 54)
CAACUGGAGCAUUUACUGC sgRNA 4 whole sequence:

(SEQ ID NO: 55)
CAACUGGAGCAUUUACUGCGUUUUAGAGCUAGAAAUAGCAAGUUAAAAUA

AGGCUAGUCCGUUAUCAACUUGAAAAAGUGGCACCGAGUCGGUGCUUUU sgRNA 5 spacer:

(SEQ ID NO: 56)
UCUUUGUAGAACUUGAAGU sgRNA 5 whole sequence:

(SEQ ID NO: 57)
UCUUUGUAGAACUUGAAGUGUUUUAGAGCUAGAAAUAGCAAGUUAAAAUA

AGGCUAGUCCGUUAUCAACUUGAAAAAGUGGCACCGAGUCGGUGCUUUU

Figure 5:
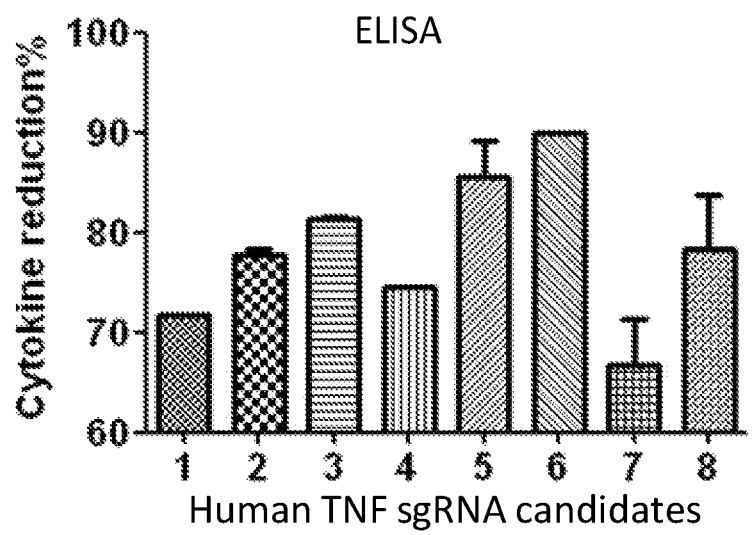
FIG. 5 is a chart showing the gene editing efficiency of various sgRNA candidates targeting the human TNF gene in Jurkat cells, using the CRISPR/CAS9 system, as compared to control cells (with no modification).

To reduce TNF production in Jurkat cells, eight sgRNAs targeting human TNF were characterized. As shown in FIG. 5, all eight sgRNAs reduced production of TNF. For example, sgRNA candidates 1-6 and 8 reduced TNF cytokine production by more than 70%.

The sequences in human TNF targeted by sgRNA 1-8 are respectively shown by double-strand sequences:

```
                                            (SEQ ID NO: 14)
5'-GAGCACTGAAAGCATGATCC-3'

(SEQ ID NO: 87)
3'-CTCGTGACTTTCGTACTAGG-5'

(SEQ ID NO: 15)
5'-GGACGTGGAGCTGGCCGAGG-3'

(SEQ ID NO: 88)
3'-CCTGCACCTCGACCGGCTCC-5'

(SEQ ID NO: 16)
5'-GAGGCGCTCCCCAAGAAGAC-3'

(SEQ ID NO: 89)
3'-CTCCGCGAGGGGTTCTTCTG-5'

(SEQ ID NO: 17)
5'-GGGGGCCCCAGGGCTCCAGG-3'

(SEQ ID NO: 90)
3'-CCCCCGGGGTCCCGAGGTCC-5'

(SEQ ID NO: 18)
5'-GCTGAGGAACAAGCACCGCC-3'

(SEQ ID NO: 91)
3'-CGACTCCTTGTTCGTGGCGG-5'

(SEQ ID NO: 19)
5'-GGCGCCTGCCACGATCAGGA-3'

(SEQ ID NO: 92)
3'-CCGCGGACGGTGCTAGTCCT-5'

(SEQ ID NO: 20)
5'-GTGCAGCAGGCAGAAGAGCG-3'

(SEQ ID NO: 93)
3'-CACGTCGTCCGTCTTCTCGC-5'

(SEQ ID NO: 21)
5'-GGAGTGATCGGCCCCCAGA-3'

(SEQ ID NO: 94)
3'-CCTCACTAGCCGGGGGTCT-5'
```

Exemplary protospacer sequences in a gRNA (e.g., a sgRNA) for targeting the above-noted human TNF sites and exemplary sgRNA sequences containing such are provided below include (respectively):

```
sgRNA 1 spacer:
                                            (SEQ ID NO: 58)
GAGCACUGAAAGCAUGAUCC sgRNA 1 whole sequence:
                                            (SEQ ID NO: 59)
GAGCACUGAAAGCAUGAUCCGUUUUAGAGCUAGAAAUAGCAAGUUAAAAU
AAGGCUAGUCCGUUAUCAACUUGAAAAAGUGGCACCGAGUCGGUGCUUUU sgRNA 2 spacer:
                                            (SEQ ID NO: 60)
GGACGUGGAGCUGGCCGAGG sgRNA 2 whole sequence:
                                            (SEQ ID NO: 61)
GGACGUGGAGCUGGCCGAGGGUUUUAGAGCUAGAAAUAGCAAGUUAAAAU
AAGGCUAGUCCGUUAUCAACUUGAAAAAGUGGCACCGAGUCGGUGCUUUU sgRNA 3 spacer:
                                            (SEQ ID NO: 62)
GAGGCGCUCCCCAAGAAGAC sgRNA 3 whole sequence:
                                            (SEQ ID NO: 63)
GAGGCGCUCCCCAAGAAGACGUUUUAGAGCUAGAAAUAGCAAGUUAAAAU
AAGGCUAGUCCGUUAUCAACUUGAAAAAGUGGCACCGAGUCGGUGCUUUU sgRNA 4 spacer:
                                            (SEQ ID NO: 64)
GGGGGCCCCAGGGCUCCAGG sgRNA 4 whole sequence:
                                            (SEQ ID NO: 65)
GGGGGCCCCAGGGCUCCAGGGUUUUAGAGCUAGAAAUAGCAAGUUAAAAU
AAGGCUAGUCCGUUAUCAACUUGAAAAAGUGGCACCGAGUCGGUGCUUUU sgRNA 5 spacer:
                                            (SEQ ID NO: 66)
GCUGAGGAACAAGCACCGCC sgRNA 5 whole sequence:
                                            (SEQ ID NO: 67)
GCUGAGGAACAAGCACCGCCGUUUUAGAGCUAGAAAUAGCAAGUUAAAAU
AAGGCUAGUCCGUUAUCAACUUGAAAAAGUGGCACCGAGUCGGUGCUUUU sgRNA 6 spacer:
                                            (SEQ ID NO: 68)
GGCGCCUGCCACGAUCAGGA sgRNA 6 whole sequence:
                                            (SEQ ID NO: 69)
GGCGCCUGCCACGAUCAGGAGUUUUAGAGCUAGAAAUAGCAAGUUAAAAU
AAGGCUAGUCCGUUAUCAACUUGAAAAAGUGGCACCGAGUCGGUGCUUUU sgRNA 7 spacer:
                                            (SEQ ID NO: 70)
GUGCAGCAGGCAGAAGAGCG sgRNA 7 whole sequence:
                                            (SEQ ID NO: 71)
GUGCAGCAGGCAGAAGAGCGGUUUUAGAGCUAGAAAUAGCAAGUUAAAAU
AAGGCUAGUCCGUUAUCAACUUGAAAAAGUGGCACCGAGUCGGUGCUUUU sgRNA 8 spacer:
                                            (SEQ ID NO: 72)
GGAGUGAUCGGCCCCCAGA sgRNA 8 whole sequence:
                                            (SEQ ID NO: 73)
GGAGUGAUCGGCCCCCAGAGUUUUAGAGCUAGAAAUAGCAAGUUAAAAUA
AGGCUAGUCCGUUAUCAACUUGAAAAAGUGGCACCGAGUCGGUGCUUUU
```

Example 3. GM-CSF Knock Out and IL6 Blocker/IL-1 Blocker-Secreting Anti-CD19 CART Cells Exerted Effective Cytotoxicity Against Nalm6 Leukemia Cells In Vivo Human T cells were transduced with a lentiviral vector encoding (i) an anti-CD19 CAR, and (ii) an anti-IL6 scFv antibody, and (iii) IL1RA. A CD8 leading sequence is located before the anti-IL6 scFv. A nucleotide sequence coding for a T2A peptide is located between the coding sequences of (i) and (ii) and a nucleotide sequence coding for a P2A peptide is located between the coding sequences of (ii) and (iii). There is a human growth hormone signal sequence located between P2A and (iii).

The anti-CD19 CAR contains, from the N-terminus to the C-terminus, a CD8 leading sequence, an anti-CD19 scFv fragment, a CD8 hinge domain, a CD8 transmembrane domain, a 4-1BB co-stimulatory domain, and a CD3ζ domain.

Exemplary amino acid sequences of domains of the anti-IL6 scFv, IL-1RA and anti-CD19 CAR used in this particular Example are provided below:

```
Anti-IL-6 scFv antibody (SEQ ID NO: 22):
EIVLTQSPATLSLSPGERATLSCSASISVSYMYWYQQKPGQAPRLLIYDM

SNLASGIPARFSGSGSGTDFTLTISSLEPEDFAVYYCMQWSGYPYTFGGG

TKVEIKGGGGSGGGGSGGGGSEVQLVESGGGLVQPGGSLRLSCAASGFTF

SPFAMSWVRQAPGKGLEWVAKISPGGSWTYYSDTVTGRFTISRDNAKNSL

YLQMNSLRAEDTAVYYCARQLWGYYALDIWGQGTTVTVSS

Human growth hormone leading sequence
(SEQ ID NO: 23):
MATGSRTSLLLAFGLLCLPWLQEGSA

IL-1RA (SEQ ID NO: 24):
RPSGRKSSKMQAFRIWDVNQKTFYLRNNQLVAGYLQGPNVNLEEKIDVVP

IEPHALFLGIHGGKMCLSCVKSGDETRLQLEAVNITDLSENRKQDKRFAF

IRSDSGPTTSFESAACPGWFLCTAMEADQPVSLTNMPDEGVMVTKFYFQE

DE

CD8 leading sequence (SEQ ID NO: 25):
MALPVTALLLPLALLLHAARP

Anti-CD19 scFv (SEQ ID NO: 26):
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEITGGGGSGGGGSGGGGSEVKLQESGPGLVAPSQSLSVTCTVSGVS

LPDYGVSWIRQPPRKGLEWLGVIWGSETTYYNSALKSRLTIIKDNSKSQV

FLKMNSLQTDDTAIYYCAKHYYYGGSYAMDYWGQGTSVTVSS

CD8 hinge domain (SEQ ID NO: 27):
TTTPAPRPPTPAPTIASQPLSLRPEACRPAAGGAVHTRGLDFACD

CD8 Transmembrane domain (SEQ ID NO: 28):
IYIWAPLAGTCGVLLLSLVITLYC 4-1BB co-stimulatory domain (SEQ ID NO: 29):
KRGRKKLLYIFKQPFMRPVQTTQEEDGCSCRFPEEEEGGCEL CD3z (SEQ ID NO: 30):
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

Six to eight weeks old NSG mice (Jackson Labs) were intravenously injected with 1×10⁶ GFP+ Nalm6 leukemia cells (ATCC). Six days later, the mice were injected with 2×10⁶ T cells expressing an anti-CD19 chimeric antigen receptor (CAR), the anti-IL-6 scFv antibody of SEQ ID NO: 22, and the IL-1RA of SEQ ID NO: 24 (anti-CD19/IL6/IL1 TCR− CART cells; 1 in FIG. 6, n=5) or T cells expressing the anti-CD19 CAR, the IL-6 blocker and IL-1RA and having the endogenous GM-CSF gene knocked out (anti-CD19/IL6/IL1 TCR−/GM-CSF− CART cells, 2 in FIG. 6, n=6). Mice not receiving the CART cells were used as controls (CTRL in FIG. 6, n=4).

Figure 6A:
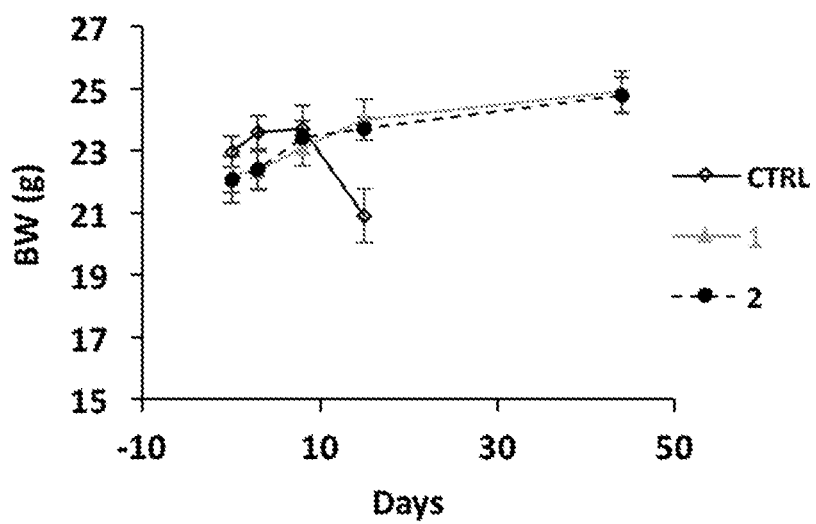
FIGS. 6A-6D are charts showing the body weight change, survival, presence of blood Nalm6 leukemia cells and human T cells in NSG mice injected with Nalm6 leukemia cells only (CTRL, n=4) or subsequently treated with CD19/IL6/IL1RA TCR– CART cells (1 in the figure, n=5) or anti-CD19/IL6/IL1RA TCR–/GM-CSF– CART cells (2 in the figure, n=6).
Figure 6B:
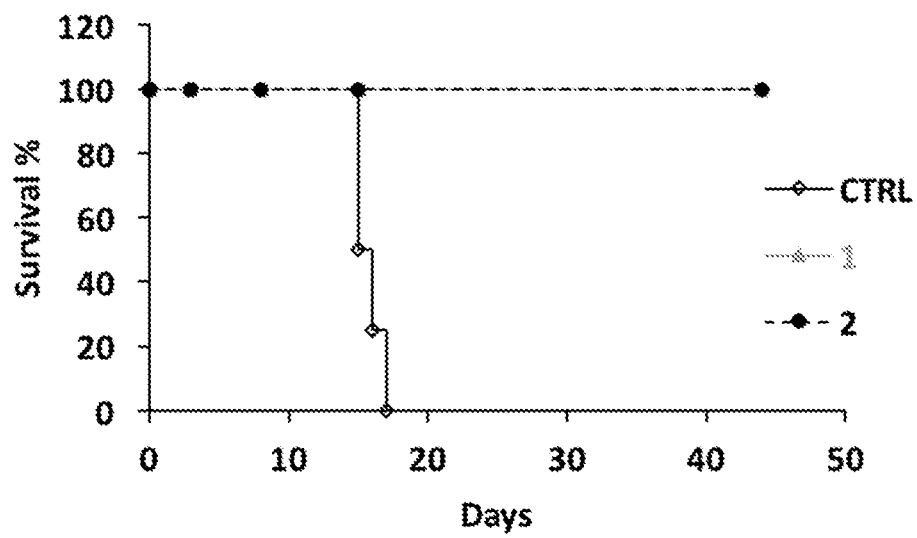

The mice were monitored for body weight, survival rate and the number of GFP+ Nalm6 leukemia cells and CD45+ CD3− T cells in the blood by Trucount beads (BD Biosciences). As shown in FIG. 6A, mice implanted with Nalm6 leukemia cells and subsequently treated with the anti-CD19/IL6/IL1RA TCR− CART cells (group 1) or the anti-CD19/IL6/IL1RA TCR−/GM-CSF− CART cells (group 2) were able to maintain their body weight 44 days post injection, whereas the control mice lost weight rapidly after 10 days. Three mice succumbed to the leukemia and one mouse was sacrificed due to apparent sickness in the control group. Likewise, the survival curves shown in FIG. 6B indicate that 100% of the mice in group 1 and 2 survived, whereas none of the mice in the control group survived past day 20.

Figure 6C:
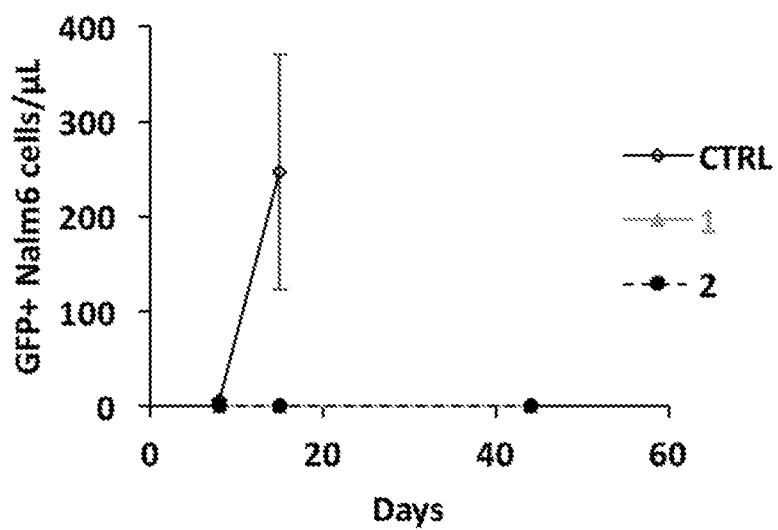

To evaluate the cytotoxicity effect of the CART cells to the Nalm6 leukemia cells, the remaining GFP+ Nalm6 cells in mice were measured. As shown in FIG. 6C, the Nalm6 leukemia cells were proliferating in the blood of the control mice throughout the course of the experiment. By contrast, little or no Nalm6 leukemia cells were detected in mice received the CART cell treatment (group 1 and 2). These results indicate that both anti-CD19/IL6/IL1RA TCR− CART cells and anti-CD19/IL6/IL1RA TCR−/GM-CSF− CART cells are capable of killing Nalm6 leukemia cells in vivo.

Figure 6D:
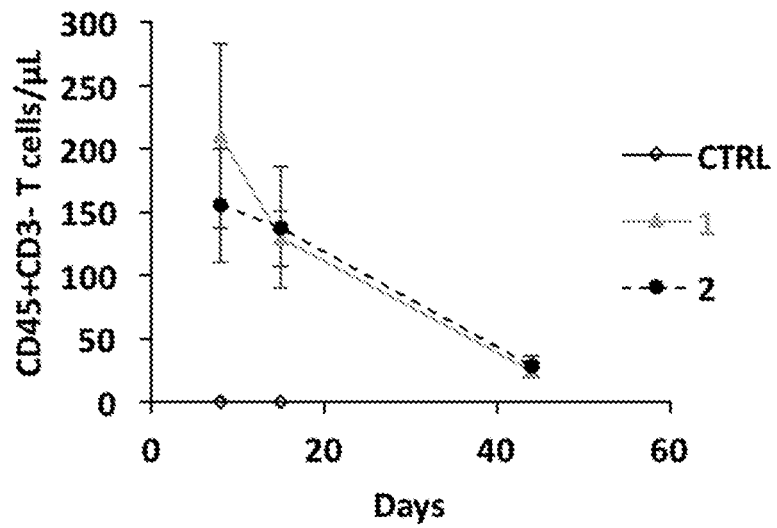

Moreover, to evaluate the property of the injected human T cells, the amount of CD45+CD3− T cells in blood of the treated mice was measured overtime. In both group 1 and 2, the level of human T cells present in blood decreased overtime, indicating that GM-CSF KO by gene editing did not transform the T cells into leukemia like cells. FIG. 6D.

Example 4: Effect of IL-2 Knock Out on T Cell Expansion

T cells showing reduction of IL-2 production after gene editing with sgRNAs 1, 3 and 5, which target IL-2, were re-stimulated with anti-CD3/CD28 beads. Sequences of sgRNAs 1, 3, and 5 are provided in Example 2 above. Subsequent T cell expansion was analyzed. T cells with electroporation of Cas9 only were included as control. No exogenous IL-2 was added during the re-stimulation.

Figure 7:
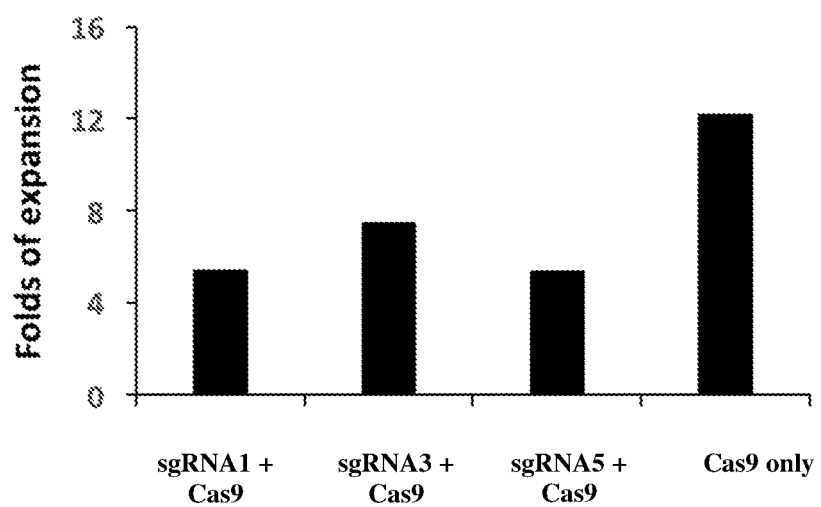
FIG. 7 is a chart showing the cellular expansion rate of T cells with reduced production of IL-2 after gene editing with sgRNA 1, 3 and 5 targeting IL-2 in response to anti-CD3/CD28 stimulation. T cells modified with Cas9 only were used as a control.

The results obtained from this study, shown in FIG. 7, indicate that T cells with IL-2 knock out were still capable of expansion but at a slightly lower rate as compared to the control group. This result indicates that T cells with IL-2 knock out were still able to propagate in vitro, and T cell proliferation at a lower rate suggests that IL-2 knock out would be effective in inhibiting T cell over proliferation induced toxicity.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A population of immune cells, comprising:
a plurality of modified immune cells, which (a) produces a reduced level of one or more inflammatory proteins as compared with wild-type immune cells of the same type under the same conditions; and
(b) expresses one or more antagonists of the one or more inflammatory proteins and/or expresses one or more immune suppressive cytokines,
wherein the one or more inflammatory proteins in (a) comprise GM-CSF, IL2, TNF, or a combination thereof;
wherein the one or more antagonists in (b) comprise IL-1RA or an antibody selected from the group consisting of tocilizumab, sirukumab, sarilumab, siltuximab, olokizumab, clazakizumab, or an antigen-binding fragment thereof, or a combination thereof;
wherein the one or more immune suppressive cytokines in (b) comprise TGFβ, IL-4, IL-10, IL-13, IL-33, IL-35, or IL-37; and
wherein the plurality of modified immune cells comprises T cells.

2. The population of immune cells of claim 1, wherein the plurality of modified immune cells express a chimeric antigen receptor (CAR) and/or an exogenous T cell receptor (TCR), wherein the CAR comprises an extracellular ligand binding domain, a transmembrane domain, and one or more intracellular signaling domains.

3. The population of immune cells of claim 2, wherein the extracellular ligand binding domain comprises a single-chain antibody fragment specific to a cell surface protein, an extracellular domain of a cytokine receptor, or an extracellular domain of a co-stimulatory receptor.

4. The population of immune cells of claim 2, wherein the one or more intracellular signaling domains comprise (i) a signaling domain of CD3ζ and/or (ii) one or more signaling domains from one or more co-stimulatory proteins or cytokine receptors.

5. The population of immune cells of claim 4, wherein the co-stimulatory proteins or cytokine receptors are selected from the group consisting of CD28, 4-1BB, 2B4, KIR, CD27, OX40, ICOS, MYD88, IL2 receptor, and SynNotch.

6. The population of immune cells of claim 2, wherein the endogenous TCR is knocked out in the modified immune cells.

7. The population of immune cells of claim 1, wherein at least one endogenous allele of the one or more inflammatory proteins in (a) is knocked out in the plurality of the modified immune cells.

8. The population of immune cells in claim 1, wherein the plurality of modified immune cells comprises one or more exogenous nucleic acid coding for the one or more immune suppressive cytokines and/or the antagonist of the one or more inflammatory proteins in (b).

9. The population of immune cells of claim 8, wherein at least one of the exogenous nucleic acids is incorporated into the genome of the modified immune cells.

10. The population of immune cells of claim 1, wherein the modified immune cells express the one or more antagonists of the one or more inflammatory proteins.

11. The population of immune cells of claim 10, wherein the antagonist comprises a single chain variable fragment (scFv) antibody that binds IL-6, and wherein the scFv antibody comprises the amino acid sequence of SEQ ID NO:22.

12. The population of immune cells of claim 10, wherein the antagonist comprises IL-1RA, which comprises the amino acid sequence of SEQ ID NO: 24.

13. The population of immune cells of claim 10, wherein the antagonists comprise an anti-IL6 scFv antibody comprising the amino acid sequence of SEQ ID NO:22 and IL-1RA comprising the amino acid sequence of SEQ ID NO:24.

14. The population of immune cells of claim 10, wherein the modified immune cells express a CAR that binds CD19.

15. A method of producing a population of immune cells with reduced inflammatory properties, the method comprising:
(i) providing a population of immune cells; and
(ii) modifying the population of immune cells to:
(a) reduce production of one or more inflammatory proteins selected from the group consisting of GM-CSF, IL2, TNF, or a combination thereof as compared with wild-type immune cells of the same type under the same conditions; and
(b) express one or more antagonists of the one or more inflammatory proteins and/or express one or more immune suppressive cytokines,
wherein (ii) comprises introducing into the population of immune cells one or more nucleic acids coding for one or more antagonists of the one or more inflammatory proteins and/or one or more immune suppressive cytokines,
wherein the one or more antagonists in (b) comprise IL-1RA or an antibody selected from the group consisting of tocilizumab, sirukumab, sarilumab, siltuximab, olokizumab, clazakizumab, or an antigen-binding fragment thereof, or a combination thereof,
wherein the one or more immune suppressive cytokines in (b) comprise TGFβ, IL-4, IL-10, IL-13, IL-33, IL-35, or IL-37, wherein the population of modified immune cells comprises T cells, and
wherein the one or more nucleic acids are in operable linkage to a promoter(s) for expression of the one or more antagonists and/or the one or more immune suppressive cytokines in the immune cells.

* * * * *

UNITED STATES PATENT AND TRADEMARK OFFICE
CERTIFICATE OF CORRECTION

| | | |
|---|---|---|
| PATENT NO. | : 11,965,176 B2 | |
| APPLICATION NO. | : 16/980237 | |
| DATED | : April 23, 2024 | |
| INVENTOR(S) | : Biliang Hu | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 606 days.

Signed and Sealed this
Eighth Day of October, 2024

Katherine Kelly Vidal
*Director of the United States Patent and Trademark Office*